(12) United States Patent
Wilhelm et al.

(10) Patent No.: US 11,583,644 B2
(45) Date of Patent: Feb. 21, 2023

(54) SPRING BRIDGE FOR A SPRING BRIDGE BREATHING BAG PLATE SYSTEM OF A CLOSED-CIRCUIT RESPIRATOR, SPRING BRIDGE BREATHING BAG PLATE SYSTEM AS WELL AS CLOSED-CIRCUIT RESPIRATOR

(71) Applicant: Dräger Safety AG & Co. KGaA, Lübeck (DE)

(72) Inventors: Christian Wilhelm, Lübeck (DE); Matthias Düpjan, Lübeck (DE); Sören Kirmse, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 291 days.

(21) Appl. No.: 16/771,619

(22) PCT Filed: Nov. 19, 2018

(86) PCT No.: PCT/EP2018/081703
§ 371 (c)(1),
(2) Date: Jun. 10, 2020

(87) PCT Pub. No.: WO2019/115159
PCT Pub. Date: Jun. 20, 2019

(65) Prior Publication Data
US 2020/0353191 A1 Nov. 12, 2020

(30) Foreign Application Priority Data
Dec. 14, 2017 (DE) .......................... 102017011581.8

(51) Int. Cl.
*A61M 16/08* (2006.01)
*A61M 16/22* (2006.01)
(Continued)

(52) U.S. Cl.
CPC .... *A61M 16/0078* (2013.01); *A61M 16/0891* (2014.02); *A61M 16/22* (2013.01); *A62B 7/00* (2013.01); *A61M 2205/07* (2013.01)

(58) Field of Classification Search
CPC .......... A61M 16/0075; A61M 16/0078; A61M 16/0081; A61M 16/0084; A61M 16/0891;
(Continued)

(56) References Cited

U.S. PATENT DOCUMENTS

| 2,420,375 | A |   | 5/1947 | Huggenberger |
| 4,266,539 | A | * | 5/1981 | Parker ...................... A62B 7/00 55/DIG. 35 |

(Continued)

FOREIGN PATENT DOCUMENTS

| AU | 8825598 A | 3/1999 |
| CN | 202086973 U | 12/2011 |

(Continued)

*Primary Examiner* — Kathryn E Ditmer
(74) *Attorney, Agent, or Firm* — McGlew and Tuttle, P.C.

(57) ABSTRACT

A spring bridge (40), for a spring bridge breathing bag plate system (80) of a closed-circuit respirator (100), includes a spring bridge carrier (42) for the arrangement of at least one spring element (82) of a spring bridge breathing bag plate system (80) and at least one fastening element (44) for holding the spring bridge (40) at the closed-circuit respirator (100). The at least one fastening element (44) is a rotating element and/or a sliding element for the rotatable and/or sliding movement of the spring bridge carrier (42) at and relative to the closed-circuit respirator (100). A spring bridge breathing bag plate system (80) is provided for a closed-circuit respirator (100) as well as for a closed-circuit respirator (100).

19 Claims, 12 Drawing Sheets

(51) Int. Cl.
*A62B 7/00* (2006.01)
*A61M 16/00* (2006.01)

(58) Field of Classification Search
CPC . A61M 16/22; A62B 7/00; A62B 7/02; A62B 7/10; A62B 9/02; A62B 19/00
See application file for complete search history.

(56) References Cited

U.S. PATENT DOCUMENTS

| | | | |
|---|---|---|---|
| 5,109,833 A * | 5/1992 | Frimberger | A61H 31/007 |
| | | | 128/205.16 |
| 2003/0213486 A1* | 11/2003 | Wang | A61M 16/0084 |
| | | | 128/202.28 |
| 2010/0236557 A1* | 9/2010 | Reisman | A61M 16/208 |
| | | | 128/205.13 |
| 2011/0120472 A1* | 5/2011 | Lee | A61M 16/0075 |
| | | | 128/205.14 |
| 2020/0376216 A1* | 12/2020 | Salman | A61M 16/0084 |

FOREIGN PATENT DOCUMENTS

| | | | | |
|---|---|---|---|---|
| CN | 105664390 A | 6/2016 | | |
| DE | 102014017955 A1 | 6/2016 | | |
| FR | 581026 A | 11/1924 | | |
| FR | 1076247 A | 10/1954 | | |
| GB | 2302561 A | 1/1997 | | |
| WO | 9907442 A2 | 2/1999 | | |
| WO | 2012073024 A2 | 6/2012 | | |
| WO | WO-2012073024 A2 * | 6/2012 | | A62B 7/00 |

* cited by examiner

SPRING BRIDGE FOR A SPRING BRIDGE BREATHING BAG PLATE SYSTEM OF A CLOSED-CIRCUIT RESPIRATOR, SPRING BRIDGE BREATHING BAG PLATE SYSTEM AS WELL AS CLOSED-CIRCUIT RESPIRATOR

CROSS REFERENCE TO RELATED APPLICATIONS

This application is a United States National Phase Application of International Application PCT/EP2018/081703, filed Nov. 19, 2018, and claims the benefit of priority under 35 U.S.C. § 119 of German Application 10 2017 011 581.8, filed Dec. 14, 2017, the entire contents of which are incorporated herein by reference.

TECHNICAL FIELD

The pertains to a spring bridge for a spring bridge breathing bag plate system of a closed-circuit respirator, having a spring bridge carrier for the arrangement of at least one spring element of a spring bridge breathing bag plate system as well as having at least one fastening element for holding the spring bridge at the closed-circuit respirator. The present invention further pertains to a spring bridge breathing bag plate system for a closed-circuit respirator, having a breathing bag plate, a spring bridge as well as at least one spring element that is arranged between the breathing bag plate and the spring bridge. Moreover, the present invention pertains to a closed-circuit respirator, having a housing with a housing lower part and with a housing upper part, a $CO_2$ absorber, an oxygen cylinder as well as a spring bridge breathing bag plate system.

TECHNICAL BACKGROUND

Breathing bags, also called counter-lungs, of many different configurations and modes of operation are usually located in closed-circuit respirators or ventilation systems for emergency or long-term ventilation of patients. These counter-lungs or breathing bags are flexible volumes, which facilitate breathing under difficult conditions or in a harmful environment.

The principle of receiving a gas quantity due to expansion or inflation and the discharge of a gas quantity due to folding in or collapsing of the gas-enclosed cover is common to all breathing bags. Here, the periodic movement may take place actively, for example, by means of auxiliary units or passively by feeding volume and removing volume.

Such auxiliary units may be, for example, spring systems of many different configurations. In this case, compression springs or tension springs can be used. In any case, the collapsing or folding in of the breathing bag is supported by the corresponding spring system. In this case, the breathing bag in conjunction with a suitable breathing bag plate forms the first mechanical counter-support of the spring system. The second counter-support, also called spring seat, is usually a u-shaped, fixed component in the closed-circuit respirator, often called spring bridge. This spring bridge assumes the support in case of the use of compression springs or the suspension in case of the use of tension springs. The spring force acting on the breathing bag plate and thus on the breathing bag surface generates a constant overpressure in the interior of the gas-enclosed cover, i.e., in the interior of the breathing bag and of the overall closed-circuit breathing system. This overpressure promotes and facilitates the breathing in, i.e., the inhalation of breathing gas, on the one hand, and at the same time protects the user of the closed-circuit breathing system against the entry of substances harmful to health as a result of the pressure direction.

The breathing bag is also needed as a collecting volume or active gas reservoir for the exhaled air purified from carbon dioxide. Based on the fact that the breathing bag has contact with breathing gas in the interior and with the surrounding area on the outer side, routine cleaning and disinfection of the breathing bag is necessary. It is thus important and necessary to clean and to disinfect the breathing bag after each use of the closed-circuit breathing system. The corresponding components in the periphery of the breathing bag must usually be removed for this purpose. The corresponding spring system must also be removed, depending on how this spring system is connected to the breathing bag. In addition, most closed-circuit respirators have a mechanical guide system and/or pneumatic connection elements, which must likewise be removed for the cleaning and disinfection process. Because of the typically confined space conditions within closed-circuit respirators, removal and mounting of the closed breathing circuit are highly complicated and very time-consuming and difficult for untrained users.

The starting position of the present invention is the breathing bag spring bridge configuration of the closed-circuit respirator of the applicant, which is used essentially for mine rescue services, but also in the area of firefighting, especially in case of long-term operations. In case of this closed-circuit respirator, mounting points for fastening a breathing bag, which are used as counter-support and the distribution of force of corresponding compression springs for the internal overpressure, are located on the upper part of the breathing bag.

FIG. 1 schematically shows a spring bridge breathing bag plate system (80) of the closed-circuit respirator (1000) of the applicant in a sectional view. The closed-circuit respirator (1000) has a housing (1020) with a housing lower part (1040) and a housing upper part (1060). The breathing bag (210) has a smaller top side (212) and a larger bottom side (214). The ports, sockets (216) for connecting the breathing bag (210) to a carbon dioxide absorber and to a breathing gas cooler unit are also shown.

The port sockets (216) must be highly stretched manually for connection to other components, so that a corresponding undercut in the socket (216) is fitted into a corresponding groove geometry in the corresponding component. Mounting points for a pressure plate (218), the so-called breathing bag plate (218), which is in turn used as counter-support and seat for the compression springs (282), are located on the top side (212) of the breathing bag (210). In interaction with the breathing bag plate (218), the compression springs (282) generate a constant overpressure in the breathing bag (210) because of the surface and force. Because of the pressure direction, this prevents the entry of harmful substances and thus protects the user of the device during breathing. The second counter-support for the two compression springs (282) forms the so-called spring bridge (240). This spring bridge is connected permanently, i.e., not detachably, to the housing bottom part (1040) in this closed-circuit respirator (1000). The installed position and periphery are shown in FIG. 1. The compression springs (282) have to be removed for removal of the breathing bag (210), for example, after using the closed-circuit respirator (1000) as a preparation for cleaning and disinfection. This is carried out by compressing the compression springs (282).

The drawbacks of this closed-circuit respirator (1000) are that there are frequently different defects in different components of the closed breathing circuit, and especially in the breathing bag (210) over the course of the lifetime of the product. This can be attributed to the technical configuration, on the one hand, and to the installed position, on the other hand, of the breathing bag (210) in the closed-circuit respirator (1000) as well as to the need for the installation and removal of the breathing bag (210) in and from the closed-circuit respirator (1000) for cleaning and disinfection. A minimum valve (not shown) located at the breathing bag (210) is very frequently damaged during the mounting and removal of the breathing bag (210). A deformed valve lever is usually a result of difficulties during the installation and removal of the breathing bag (210). The breathing bag (210) itself may also be slightly damaged. This can be attributed, among other things, to confined space conditions and connection principles. Since the spring bridge (240) is a permanently installed component at the lower device housing (1020), it does not make possible barrier-free work within the closed-circuit respirator (1000). To be able to reach the compression springs (282) between the breathing bag (210) and the spring bridge (240), some and preferably all other components must be removed from the device interior beforehand, since the movement spaces are very restricted for the hands of the technician. After the absorber and breathing air cooler of the closed-circuit respirator (1000) are removed, the breathing bag (210) can be removed by removing the minimum bag. Another drawback is the need to remove the breathing bag guide. This metallic lever is directly fastened at one end to the breathing bag plate (21) by means of a snap fastener and is movably mounted on the opposite side outside of the spring bridge breathing bag plate system.

It is very often necessary to disassemble, to clean and then to reassemble and to check many closed-circuit respirators because of extensive operation scenarios. This usually occurs in large firefighting operations with many firefighters for the use of closed-circuit respirators. Because of the hazardous situation and the limited number of closed-circuit respirators, it is very often necessary to prepare used closed-circuit respirators again for the new operation as rapidly as possible. This has to be done only by very highly qualified and trained staff in case of the above-described closed-circuit respirator of the applicant. All manual actions cannot be compared to such manual actions from daily life. Intuitive use and operation are thus almost ruled out.

SUMMARY

Based on this state of the art, a basic object of the present invention is to at least partly eliminate these drawbacks of spring bridge breathing bag plate systems of a closed-circuit respirator and thus of a closed-circuit respirator. Therefore, the object of the present invention is to provide a spring bridge for a spring bridge breathing bag plate system of a closed-circuit respirator, a spring bridge breathing bag plate system for a closed-circuit respirator as well as a closed-circuit respirator, which make possible the mounting and removal of a breathing bag of a closed-circuit respirator in a simple and rapid manner for cleaning purposes. In particular, a reduced number of individual components and more space for maintenance procedures shall be created within the closed-circuit respirator in the area of the spring bridge breathing bag plate system.

The above object is accomplished by a spring bridge for a spring bridge breathing bag plate system of a closed-circuit respirator with features according to the invention, by a spring bridge breathing bag plate system for a closed-circuit respirator with the features according to the invention as well as by a closed-circuit respirator with the features according to the invention. Further features and details of the present invention appear from the subclaims, from the specification and from the drawings. The features and details herein, which are described in connection with the spring bridge according to the present invention, apply, of course, also in connection with the spring bridge breathing bag plate system according to the present invention as well as with the closed-circuit respirator according to the present invention, and vice versa, so that reference is and can always be mutually made to the individual aspects of the present invention with regard to the disclosure.

According to the present aspect of the present invention, the object is accomplished by a spring bridge for a breathing bag of a closed-circuit respirator, having a spring bridge carrier for the arrangement of at least one spring element of a spring bridge breathing bag plate system as well as having at least one fastening element for holding the spring bridge at the closed-circuit respirator. The spring bridge is characterized in that the at least one fastening element is a rotating element and/or a sliding element for the rotatable and/or sliding movement of the spring bridge at and relative to the closed-circuit respirator.

A spring bridge configured in this manner for a spring bridge breathing bag plate system for a closed-circuit respirator makes possible a simple and rapid mounting as well as removal of a breathing bag of a closed-circuit respirator, which breathing bag is arranged under the spring bridge. Because of the special configuration of the at least one fastening element, the spring bridge held at a closed-circuit respirator can be rotated and/or displaced as a rotating element and/or as a sliding element in a very simple manner from a working position into an opened position in order to thus release the access to the breathing bag. In the working position, the spring bridge is used as a counter-support for spring elements, which are arranged between the spring bridge and the breathing bag. In other words, in the working position, the spring bridge is used as a support of the compression springs or tension springs. In the working position, the spring bridge is arranged immovably, preferably locked at the closed-circuit respirator.

The spring bridge is preferably arranged within the closed-circuit respirator in the working position parallel to the top side of the breathing bag. Consequently, the spring elements of the spring bridge breathing bag plate system, which spring elements are supported at the spring bridge, exert a spring force on the breathing bag. Based on the configuration of the fastening element as a rotating element and/or sliding element, the spring bridge can be transferred from the working position into a so-called opened position by means of a rotating movement and/or sliding movement. In other words, the spring bridge can preferably be rotated or pivoted by means of the rotating element in relation to the closed-circuit respirator or in relation to the housing of the closed-circuit respirator to thus release the access to the breathing bag arranged under the spring bridge in the working position.

As an alternative or in addition to the rotating movement, the spring bridge can be displaced into an opening position by means of the at least one sliding element in order to thus release the access to the breathing bag arranged under the spring bridge. Due to the rotatability or displaceability of the spring bridge in relation to a closed-circuit respirator or in relation to the housing of a closed-circuit respirator, a technician can reach the breathing bag of the closed-circuit respirator in a simple and rapid manner for cleaning purposes or for removal purposes.

Because the at least one fastening element is arranged as a rotating element and/or sliding element at the spring bridge, the spring bridge can be pivoted or displaced in a very simple and rapid manner in relation to the closed-circuit respirator in order to thus release access to the breathing bag. The at least one fastening element of the spring bridge is preferably arranged, especially in a rotationally movable manner, at a counter-fastening element of the closed-circuit respirator. The counter-fastening element is preferably mounted in a rotatable and/or displaceable manner on an inner wall of a housing, especially a device lower shell or a device lower part, of the closed-circuit respirator.

The spring bridge is preferably configured as a U-shaped section, wherein the spring bridge carrier forms the bottom of the section with the U-shaped configuration and a fastening element in the form of a rotating element and/or of a sliding element is arranged at the free ends of the two legs of the U-shaped section each. An especially simple pivotability or displaceability of the spring bridge in relation to the housing of a closed-circuit respirator is guaranteed as a result.

A spring bridge configured in this manner creates more space for maintenance procedures within the closed-circuit respirator, especially at a spring bridge breathing bag plate system of the closed-circuit respirator or at a breathing bag of the closed-circuit respirator because of the movability of the spring bridge from a working position into an opened position. The breathing bag under the spring bridge breathing bag plate system is readily accessible in the opened position of the spring bridge and thus of the spring bridge breathing bag plate system and in this opened position can be very easily removed for cleaning purposes or for replacement purposes. The mounting of the cleaned or new breathing bag into the closed-circuit respirator is correspondingly simple if the spring bridge and thus the spring bridge breathing bag plate system are located in the opened position.

According to a preferred variant of the present invention, provisions may be made in a spring bridge for the fastening element or the rotating element to be a rotary joint, a universal joint, an angular element, a ball and socket joint, a hinge element or a receptacle for fastening to a pin of the closed-circuit respirator. Rotating elements configured in this manner make possible an especially simple rotation or pivoting of the spring bridge in relation to the housing of the closed-circuit respirator and thus a simple and rapid accessibility of the breathing bag of the closed-circuit respirator, which breathing bag is arranged under the spring bridge in the working position. The spring bridge can be configured such that it has a single fastening element, especially a single rotating element, by means of which the spring bridge can be moved back and forth between the working position and the opened position. A section, at the end of which the one fastening element is arranged, can, for example, be arranged bent at an angle at the spring bridge carrier of the spring bridge. This one fastening element can be arranged rotatably at a corresponding counter-fastening element, for example, in a pivotingly movable manner at a pin at the housing of the closed-circuit respirator. However, a spring bridge especially preferably has two fastening elements, by means of which the spring bridge is mounted in a pivotingly movable manner at corresponding counter-fastening elements of the housing of a closed-circuit respirator, especially of the housing lower part of a closed-circuit respirator.

Provisions may preferably further be made in a spring bridge for the at least one fastening element to be arranged at at least one cantilever of the spring bridge, wherein the at least one cantilever is arranged at the spring bridge carrier bent at an angle to the spring bridge carrier. A spring bridge, in which two cantilevers are arranged bent at an angle to the spring bridge carrier on two opposite sides of the spring bridge carrier, is especially advantageous. The two cantilevers together with the spring bridge carrier particularly form a U-shaped or approximately U-shaped section. Fastening elements, preferably rotating elements, by means of which the spring bridge can be mounted in a rotatable or pivotingly movable manner at corresponding counter-fastening elements of the housing of the closed-circuit respirator, are each arranged at the free ends of the cantilevers. A spring bridge of such a configuration can be rotated or pivoted, for example, in a simple manner by a 90° rotation or an approximately 90° rotation from the working position into the opened position, so that in the opened position the spring bridge or the spring bridge carrier of the spring bridge extends vertically or approximately vertically to the housing bottom side of the closed-circuit respirator. As a result, a breathing bag, which was covered by the spring bridge in the working position, is freely accessible.

Receptacles, which are connected rotationally to one another with counter-fastening elements of the housing wall of the closed-circuit respirator, which counter-fastening elements are correspondingly configured as pins, are preferably provided as rotating elements at the end of the cantilevers facing away from the spring bridge carrier. Unlike the prior-art spring bridge breathing bag plate system, a spring bridge having such a configuration makes possible a folding of the spring bridge and even a removal of the spring bridge from the closed-circuit respirator. The advantage thus arises for a user of gaining space for all other activities which are necessary to maintain the closed-circuit respirator. The spring bridge is no longer permanently arranged fixed, especially riveted, to the lower shell of the device, as in case of the prior-art spring bridge breathing bag plate system, but rather is held movably and/or removable at the lower shell of the device. Especially due to the configuration of the rotating elements as receptacles, the spring bridge can be rotated both about pins, which form the counter-fastening elements for the receptacles, and be removed from same in a simple manner by overcoming a clamping force. Consequently, an especially simple accessibility to the breathing bag of the closed-circuit respirator is made possible, so that this breathing bag can be removed by a user from the closed-circuit respirator and correspondingly cleaned.

According to a preferred variant of the present invention, provisions may be made in a spring bridge for the sliding element to be a guide link or a guide pin for guiding the spring bridge at a counter-sliding element, especially at a counter-guide pin or at a counter-guide link, of the closed-circuit respirator. This makes possible a displacement, especially linear displacement of the spring bridge in relation to the closed-circuit respirator. Due to the displacement of the spring bridge from the working position into an opened position or into an intermediate opened position, additional space can be created for the mounting and removal of a breathing bag of a closed-circuit respirator. The at least one sliding element can also be configured, for example, as a telescopic guide, by means of which the spring bridge can be displaced in a linearly displaceable manner between the working position and the opened position or an intermediate opened position. A sliding element each is preferably provided at the two cantilevers of a spring bridge having a U-shaped configuration.

According to an especially preferred variant of the present invention, provisions may be made in a spring bridge for the spring bridge to have at least one holding element for holding the spring bridge in a working position and for holding the spring bridge in an opened position. Due to the holding element or the holding elements, the spring bridge can be held in the particular position in relation to the housing of the closed-circuit respirator. In other words, in the working position, the holding element holds the spring bridge fixed in relation to the housing of the closed-circuit respirator, so that the spring bridge forms the counter-support for the spring elements of a spring bridge breathing bag plate system. The at least one holding element is preferably configured as a snap-in element or as a clamping element. In other words, the holding element is or the holding elements are preferably configured such that device readiness is represented by snapping in or clamping in the working position and the removal of the spring bridge for maintenance is made possible in a facilitated manner by snapping in or clamping in the opened position. In both positions, the spring bridge can be held immovably in relation to closed-circuit respirator because of the holding element or holding elements.

Especially preferred is a spring bridge, in which the spring bridge carrier has a locking device for locking a breathing bag plate of the spring bridge breathing bag plate system at the spring bridge carrier, which breathing bag plate is acted on by spring force by the at least one spring element of the spring bridge breathing bag plate system. In other words, the locking device is used to fix the breathing bag plate of a spring bridge breathing bag plate system at the spring bridge carrier of the spring bridge. Such a locking device is used to optimize the installation and removal of the spring bridge or of the spring bridge breathing bag plate system in and from the closed-circuit respirator. To remove the spring bridge or the spring bridge breathing bag plate system, the breathing bag plate of the spring bridge breathing bag plate system, which is arranged directly but detachably on the breathing bag is pulled in the direction of the spring bridge carrier and locked with the locking device of the spring bridge, and especially snapped in or clamped. To lock the breathing bag plate at the spring bridge carrier, the at least one spring element of the spring bridge breathing bag plate system, especially the two compression springs, is compressed to a minimum, so that a very compact unit, comprising the spring bridge, breathing bag plate and at least one spring element, results. This compact unit, which basically represents the spring bridge breathing bag plate system, can be rotated or displaced and possibly removed from the closed-circuit respirator because of the at least one rotating element and/or sliding element in a simple movement sequence. Thus, a free access to the breathing bag of the closed-circuit respirator and all other components within the closed-circuit respirator is ensured in a simple manner. In the opened position of the spring bridge, the breathing bag may be removed in a simple manner from the spring bridge breathing bag plate system, especially from the breathing bag plate of the spring bridge breathing bag plate system and be correspondingly cleaned. The mounting of the spring bridge and thus of the spring bridge breathing bag plate system at the closed-circuit respirator is carried out in the reverse sequence. The spring bridge or compact unit of the spring bridge breathing bag plate system is fastened in a pivotingly movable manner and/or in a sliding manner by means of the at least one fastening element to the counter-fastening element of the housing wall of the closed-circuit respirator and is folded or displaced from the opened position into the working position and is locked there by means of the holding element. After the spring bridge has reached the working position and is snapped in or clamped in this working position, the locking device can be detached, so that the breathing bag plate of the spring bridge breathing bag plate system can find its position at the breathing bag and can exert a corresponding spring force on the breathing bag because of the spring force of the at least one spring element.

In a preferred variant of the present invention, provisions may be made in case of a spring bridge for the locking device to be mounted in a pivoting manner at the spring bridge carrier via a pivot axis, especially such that the locking device extends flatly or approximately flatly to the spring bridge carrier in a released position, in which the breathing bag plate of the spring bridge breathing bag plate system is not held by means of the locking device at the spring bridge carrier, and the locking device extends sloped, especially vertically, toward the spring bridge carrier in a locked position, in which the breathing bag plate of the spring bridge breathing bag plate system is held at the spring bridge carrier by means of the locking device. Due to a spring bridge having such a configuration, a user can already recognize whether or not the breathing bag plate of the spring bridge breathing bag plate system is fixed to the spring bridge by the position of the locking device relative to the spring bridge carrier. In other words, the locking device, which is preferably configured as a locking lever, is configured in terms of size and folding direction such that in case the locking device is set up, i.e., if the breathing bag plate is locked and held, it is not possible to close the housing cover, i.e., the housing upper part of a closed-circuit respirator. As a result, the user is forced to check the closed breathing circuit of the closed-circuit respirator, which ultimately increases the safety of the overall closed-circuit respirator. A use of the closed-circuit respirator with breathing bag plate locked at the spring bridge carrier is not possible.

The locking device is preferably configured as a snap-in element or clamping element. A quarter-turn fastener is possible as well. In the released position of the locking device, the locking device preferably extends parallel or flatly to the spring bridge carrier of the spring bridge. In this released position, the locking device does not extend behind the breathing bag plate, so that this breathing bag plate remains arranged freely movable in relation to the spring bridge. In the locked position, the locking device extends behind the breathing bag plate and as a result holds this breathing bag plate fixed to the spring bridge carrier of the spring bridge. The locking device is mounted in a pivoting manner about a pivot axis at the spring bridge carrier, so that this locking device can be transferred in a simple manner from the released position into a locked position and vice versa. The locking device is preferably arranged centrally at or in the spring bridge carrier of the spring bridge. The breathing bag plate thus can be held centered at the spring bridge carrier.

For cleaning purposes, a user of the closed-circuit respirator can manually move the breathing bag plate against the spring force of the at least one spring element of the spring bridge breathing bag plate system in the direction of the spring bridge carrier of the spring bridge and can then lock the breathing bag plate at the spring bridge carrier by pivoting the locking device from the released position into the locked position. The locking device is configured here such that this locking device holds the breathing bag plate fixed at the spring bridge in the locked position, so that this spring bridge cannot easily spring back into a starting position because of the compression of the at least one spring element. The thus resulting, highly compact unit comprising the spring bridge, breathing bag plate and at least one spring element can be pivoted in an especially simple manner and/or be displaced relative to the housing of a closed-circuit respirator in order to thus guarantee a simple accessibility to the breathing bag of the closed-circuit respirator. The especially vertical arrangement of the locking device or of the locking lever at the spring bridge carrier in the locked position ensures that a housing top side of the closed-circuit respirator cannot be mounted on the device bottom side of the closed-circuit respirator. Only if the locking device was transferred from the locked position into the released position and thus the movement of the breathing bag plate was again released, the housing upper part of the closed-circuit respirator can be mounted at the housing bottom part of the closed-circuit respirator. A check of the functional reliability of the spring bridge breathing bag plate system and thus of the closed-circuit respirator is ensured as a result. Due to the special arrangement and functionality of such a locking device of a spring bridge, the user is forced to check the closed breathing circuit, which ultimately increases the safety of the overall closed-circuit respirator. Using the closed-circuit respirator with locked breathing bag plate is not possible.

A spring bridge breathing bag system has at least one spring element, which is arranged between the breathing bag plate and the spring bridge or the spring bridge carrier of the spring bridge. The at least one spring element may have a different configuration. A spring bridge breathing bag system especially preferably has two tension springs. In order to securely hold such compression springs or tension springs at the spring bridge, a spring bridge is preferred, in which the spring bridge carrier has at least one first receiving element for arrangement of at least one first end of the at least one spring element of the spring bridge breathing bag system. In other words, a so-called mounting geometry for an end of the compression springs or tension springs of the spring bridge breathing bag system is located on the side of the spring bridge carrier facing the breathing bag. The mounting geometry or the first receiving element can be a ring-shaped groove or a cylindrical projection, for example, a sleeve-like or pot-like projection. The at least one receiving element is used as counter-support for the at least one spring element and thus holds the at least one spring element in a defined position relative to the spring bridge carrier of the spring bridge. The at least one spring element can, in addition, be held by means of fixing elements at the first receiving element of the spring bridge carrier. It is especially advantageous when the at least one first receiving element is configured for the positive-locking holding of the at least one spring element of the spring bridge breathing bag system. For example, plug-in elements, such as pins or split pins, can be used as fixing elements.

According to a second aspect of the present invention, the object is accomplished by a spring bridge breathing bag plate system for a closed-circuit respirator, having a breathing bag plate, a spring bridge as well as at least one spring element that is arranged between the breathing bag plate and the spring bridge. The spring bridge breathing bag plate system is characterized in that the spring bridge is configured in accordance with the above-described first aspect of the present invention, especially in accordance with claims 1 through 8. A spring bridge breathing bag plate system configured in this manner for a closed-circuit respirator makes possible an especially simple movement of the spring bridge breathing bag plate system between a working position and an opened position and thus a simple mounting and removal of a breathing bag from the spring bridge breathing bag plate system or from the closed-circuit respirator. This is guaranteed by the spring bridge and correspondingly the spring bridge breathing bag plate system being able to be arranged pivotingly and slidingly at the housing of a closed-circuit respirator. The advantages, which were described in detail with regard to the spring bridge according to the first aspect of the present invention, also apply, of course, to the spring bridge breathing bag plate system according to the second aspect of the present invention.

Because the spring bridge can be pivoted or displaced relative to the housing of the closed-circuit respirator and possibly be removed from the housing because of the at least one fastening element of the spring bridge, an especially simple removal of the breathing bag of the closed-circuit respirator from the housing of the closed-circuit respirator is guaranteed. The breathing bag plate is detachably fastened to the breathing bag, so that the breathing bag is freely accessible to a user for removal from the closed-circuit respirator after pivoting of the unit, comprising the spring bridge, the at least one spring element and the breathing bag plate. The at least one spring element of the spring bridge breathing bag plate system may have a different configuration. For example, the at least one spring element can be configured as compressible elastomer or rubber. The at least one spring element is especially preferably configured as a compression spring or tension spring. The spring bridge breathing bag plate system preferably has two compression springs or tension springs extending parallel to one another. The respective first ends of the compression springs or tension springs are held at the spring bridge carrier in a positive-locking manner and possibly, in addition, in a forced fit manner. The respective second ends of the spring elements are arranged in a positive-locking manner and here as well possibly, in addition, in a forced fit manner at the breathing bag plate. The spring elements are preferably configured such that these spring elements makes possible a compression in the direction of the longitudinal axis of the spring elements, but prevent a pivoting of the spring elements relative to the longitudinal axis of the spring elements as much as possible. A certain dimensional stability of the spring elements is ensured as a result. A different configuration of the compression springs or tension springs, which are optimized with regard to buckling and linear compression and decompression paths, is also conceivable. For example, the spring elements can be configured as compression springs or as tension springs having a rectangular spring wire cross section. Springs of this configuration especially support linear compression and decompression paths. The breathing bag plate is detachably arranged on the breathing bag top side of the breathing bag. This can be carried out, for example, by means of magnets, snap fasteners, straps or positive-locking geometries.

According to a preferred variant of the present invention, provisions may be made in case of a spring bridge breathing bag plate system for one or more stabilizing elements to be arranged between the breathing bag plate and the spring bridge carrier of the spring bridge for the defined up and down movement of the breathing bag plate and thus of the breathing bag in the direction away from and toward the spring bridge. In other words, the at least one stabilizing element prevents a buckling of the at least one spring element, especially of the two compression springs, in case of compression, i.e., in case of increasing breathing bag volume. In order to prevent buckling of the at least one spring element, the breathing bag plate is preferably connected linearly to two wire straps configured as stabilizing elements and rotationally to the spring bridge. Due to the stabilizing elements, a defined up and down movement of the breathing bag plate and thus of the breathing bag in all orientations of the closed-circuit respirator is made possible. The at least one stabilizing element is preferably configured such that this stabilizing element makes possible only a linear movement or only an approximately linear movement of the breathing bag plate in the direction of the spring bridge carrier or from the direction of the spring bridge carrier. As a result, it can be guaranteed that the breathing bag fastened to the breathing bag plate is compressed and decompressed in a defined manner. The at least one stabilizing element may also have a different configuration in addition to wire straps. For example, one or more scissor hinges or a guide arm may be provided with a center of rotation located geometrically outside of the spring bridge. Corresponding receptacles for the at least one stabilizing element may be provided both at the spring bridge, i.e., especially at the spring bridge carrier, and at the breathing bag plate. These receptacles hold the at least one stabilizing element securely between the spring bridge carrier and the breathing bag plate, so that functionality of the at least one stabilizing element is guaranteed.

Provisions may preferably be made in a spring bridge breathing bag plate system for the breathing bag plate to have at least one second receiving element for arrangement of at least one second end of the at least one spring element of the spring bridge breathing bag plate system. It is consequently ensured that the at least one spring element, preferably spring elements configured as compression springs or tension springs, is arranged securely at the breathing bag plate. The at least one second receiving element may be, for example, a ring-shaped groove, a tubular or sleeve-like projection or a projection in the form of a pot or pin at the breathing bag plate. In addition, fixing elements, for example, in the form of small pins, may be provided for the positive-locking holding of the at least one spring element at the breathing bag plate in order to guarantee a better hold, especially a forced fit hold, of the at least one spring element at the breathing bag plate or at the at least one second receiving element of the breathing bag plate.

According to a third aspect of the present invention, the object is accomplished by a closed-circuit respirator, having a housing with a housing lower part and with a housing upper part, a breathing bag, a $CO_2$ absorber, an oxygen cylinder as well as a spring bridge breathing bag plate system. According to the present invention, the spring bridge breathing bag plate system of the closed-circuit respirator is configured in accordance with the second aspect of the present invention, and especially in accordance with one of the above claims 9 through 12. Such a closed-circuit respirator has the same advantages as they were described in detail according to the spring bridge according to the first aspect of the present invention and of the spring bridge breathing bag plate system according to the second aspect of the present invention.

A closed-circuit respirator having such a configuration can undergo maintenance or be cleaned after a use in an especially simple manner. The breathing bag of the closed-circuit respirator is especially accessible in an especially simple manner because of the pivotability and/or rotatability of the spring bridge of the spring bridge breathing bag plate system. After a use of the closed-circuit respirator, for example, in case of a fire, the spring bridge or the unit comprising the spring bridge, the spring element(s) and the breathing bag plate, i.e., the spring bridge breathing bag plate system, can be transferred in a simple manner from a working position into an opened position and possibly be entirely removed from the housing of the closed-circuit respirator, so that a user can in a rapid and easily accessible manner remove the breathing bag from the closed-circuit respirator in order to clean same.

Provisions may preferably be made in case of a closed-circuit respirator for the housing, especially the housing lower part, to have at least one counter-fastening element for the rotatable and/or sliding holding of the spring bridge and thus of the spring bridge breathing bag plate system at the closed-circuit respirator by means of the at least one fastening element of the spring bridge. The at least one counter-fastening element may be, for example, a pin, which protrudes on the inner side of the housing wall of the lower part of the housing of the closed-circuit respirator. Corresponding fastening elements, especially in the form of receptacles, of the spring bridge make possible both a pivoting of the spring bridge relative to the housing of the closed-circuit respirator and a simple removal of the spring bridge from the closed-circuit respirator. As a result, an especially rapid and easy accessibility to the breathing bag is guaranteed.

According to an especially preferred variant of the present invention, provisions may be made in case of a closed-circuit respirator for two opposite sides of the housing, especially sides of the housing lower part, to have a counter-fastening element each for receiving two fastening elements of the spring bridge carrier. Due to such a configuration of the closed-circuit respirator, an especially good and secure connection of the spring bridge to the housing of the closed-circuit respirator is guaranteed; in particular, the spring bridge or the spring bridge breathing bag plate system is thus also used as a stabilizing element within the closed-circuit respirator, since it connects two opposite walls of the housing lower part of the closed-circuit respirator to one another and thus acts in a reinforcing manner as support element under the housing upper part.

According to another variant of the present invention, provisions may be made in a spring bridge breathing bag plate system for the breathing bag to have one or more projections; in particular, the breathing bag has a circumferential collar on the breathing bag top side, at which or in which the breathing bag plate can be mounted in a positive-locking manner. It is consequently ensured that the breathing bag plate is arranged in a defined position in relation to same. The breathing bag plate is especially preferably detachably fastened to the top side of the breathing bag by means of magnets, snap fasteners, straps or positive-locking geometries.

Further features which improve the present invention appear from the following description of exemplary embodiments of the present invention, which are shown in the figures. All the features and/or advantages appearing from the claims, from the description and from the drawings, including structural details and arrangements in space, may be essential to the present invention both in themselves and in the different combinations. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
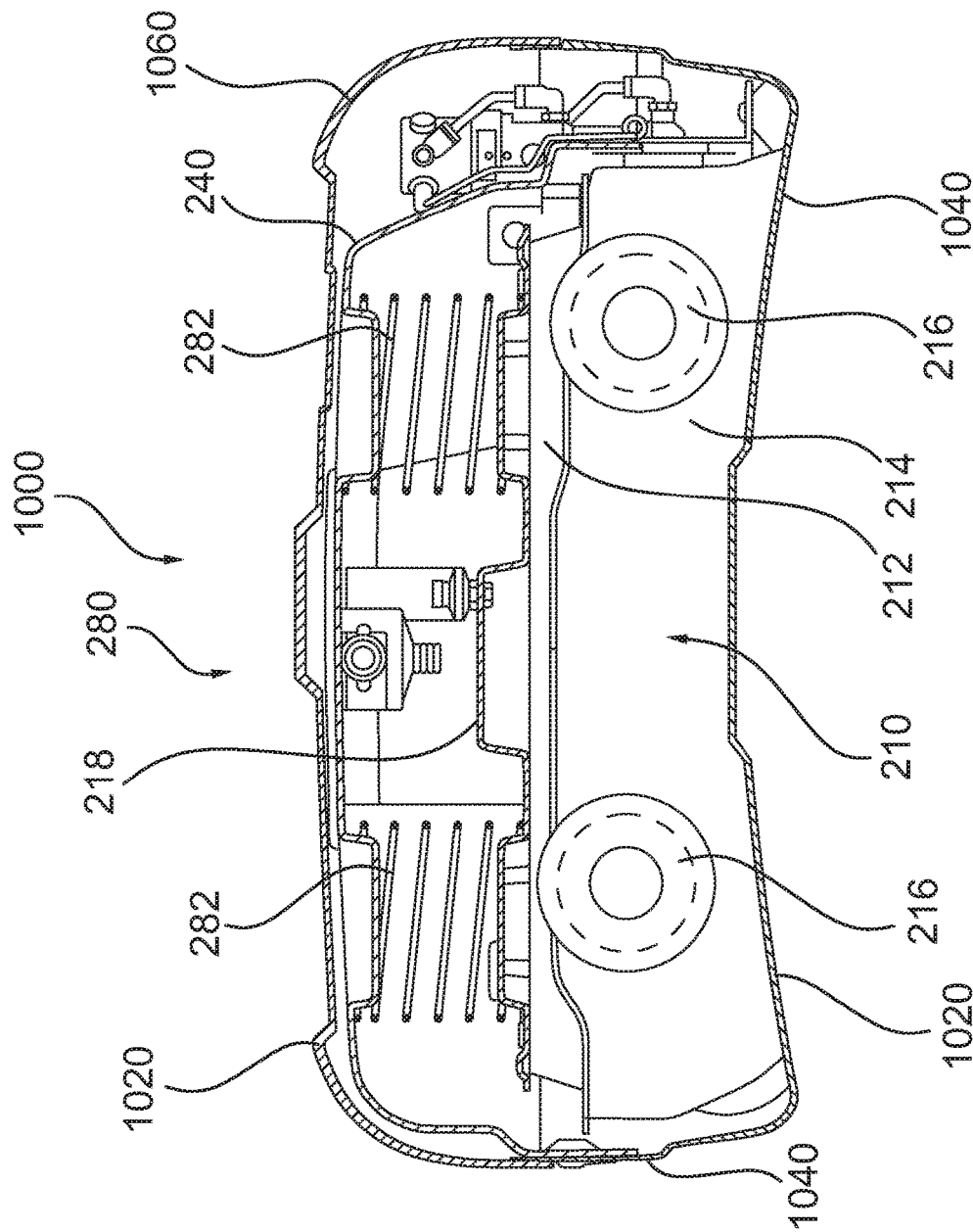
FIG. 1 is a sectional schematic view showing a spring bridge breathing bag plate system of a prior-art closed-circuit respirator.
Figure 2:
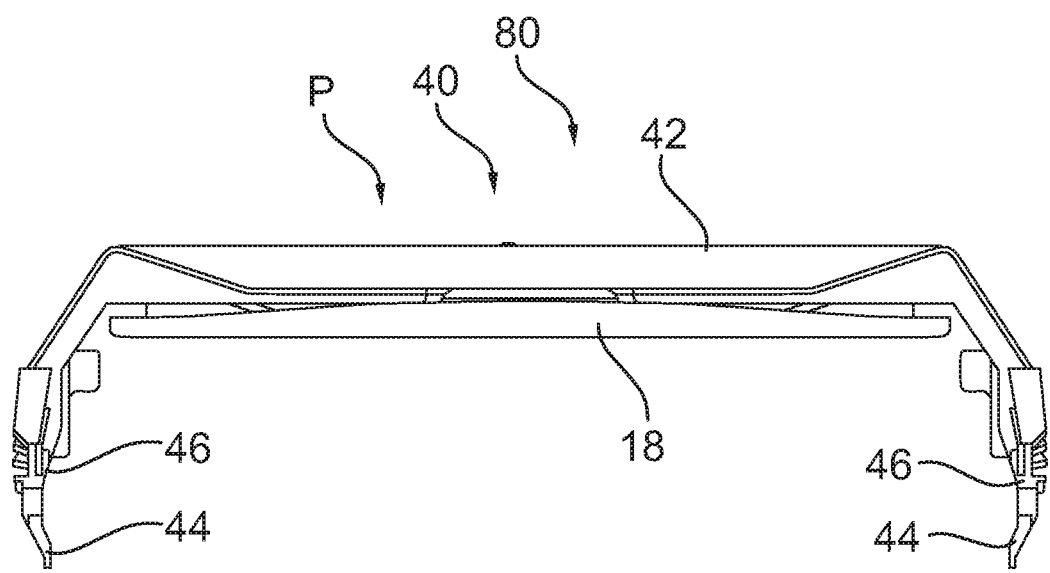
FIG. 2 is a schematic side view showing a spring bridge breathing bag plate system according to the present invention for a closed-circuit respirator.
Figure 3:
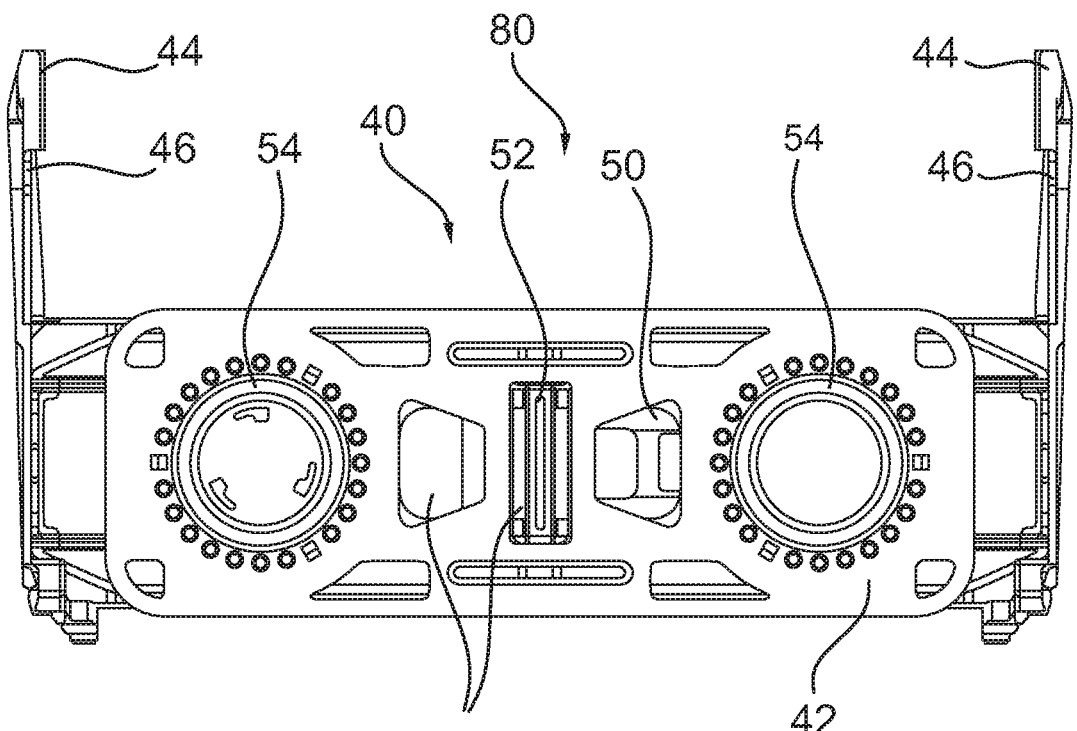
FIG. 3 is a bottom schematic view showing the spring bridge breathing bag plate system according to FIG. 2 in a view from below.

Referring to the drawings, FIG. 2 schematically shows in a side view a spring bridge breathing bag plate system 80 according to the present invention for a closed-circuit respirator. FIG. 3 schematically shows the spring bridge breathing bag plate system 80 shown in FIG. 2 in a view from below. The spring bridge breathing bag plate system 80 has a spring bridge 40 with a spring bridge carrier 42, two spring elements 82 as well as a breathing bag plate 18. In the view of the spring bridge breathing bag plate system 80 shown in FIG. 2, the breathing bag plate 18 is brought as close as possible to the spring bridge carrier 42 of the spring bridge 40, wherein the two spring elements 82 are highly compressed such that they are not visible in FIG. 2. In this locked position P, the breathing bag plate 18 is fixed to the bottom side of the spring bridge carrier 42 by means of the locking device 50, not shown. A breathing bag 10 of a closed-circuit respirator 100 could be easily removed from the breathing bag plate 18 in the locked position P. The spring bridge 40 has a section with a yoke-like or U-shaped configuration. Cantilevers 46, which form the legs of the U-shaped section of the spring bridge 40, are each arranged on two opposite sides of the spring bridge carrier 42. The cantilevers 46 are arranged at the spring bridge carrier 42 bent at an angle to the spring bridge carrier 42. A fastening element 44 in the form of a rotating element is arranged each at the free ends of the two cantilevers 46. The rotating element 44 may be, for example, a rotary joint, a universal joint, a ball and socket joint or a hinge element. The rotating element 44 is preferably a receptacle for the rotational fastening to a pin configured as a counter-fastening element 48 at a housing inner wall of a housing 102 of a closed-circuit respirator 100. Due to fastening elements 44 having such a configuration, the spring bridge 40 can be pivoted in a simple manner from a working position A into an opened position O. The spring bridge 40 is preferably pivoted by 90° or by approximately 90° about the axis of rotation of the two rotating elements 44. As a result, an access to the breathing bag 10 of a closed-circuit respirator 100, which breathing bag is arranged in the working position A under the spring bridge 40, can be guaranteed in a simple and rapid manner. The breathing bag 10 can then very simply be removed from the closed-circuit respirator 100 for cleaning purposes. The breathing bag plate 18 of the spring bridge breathing bag plate system 80 has first receiving elements 54 for receiving spring elements 82, which are configured especially as compression springs or tension springs. The first receiving elements 54 are preferably configured for the positive-locking holding of the spring elements 82 of the spring bridge breathing bag system 80. For example, plug-in elements, such as pins or split pins, may, in addition, be used as fixing elements for fixing the spring elements 82 to the first receiving elements 54.

Figure 4:
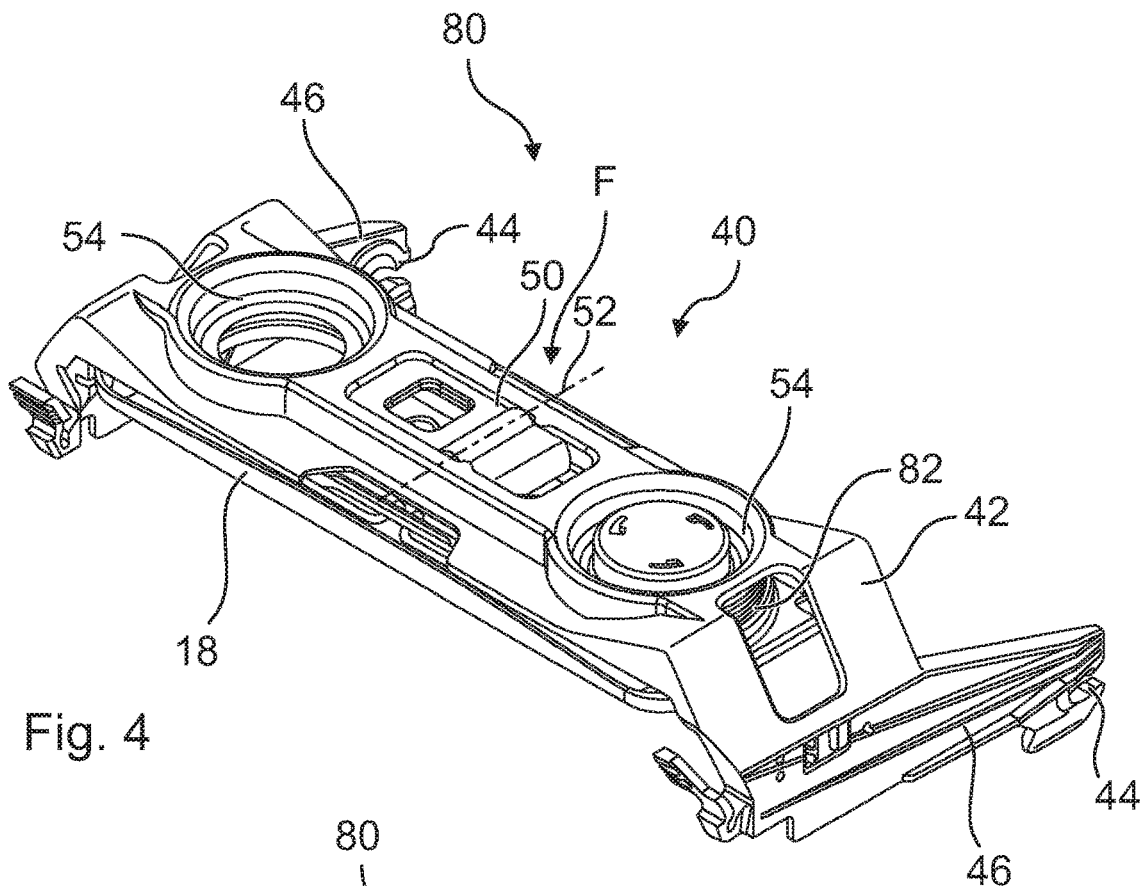
FIG. 4 is a schematic perspective view of the spring bridge breathing bag plate system according to FIG. 2, wherein the locking device of the spring bridge is in a released position.
Figure 5:
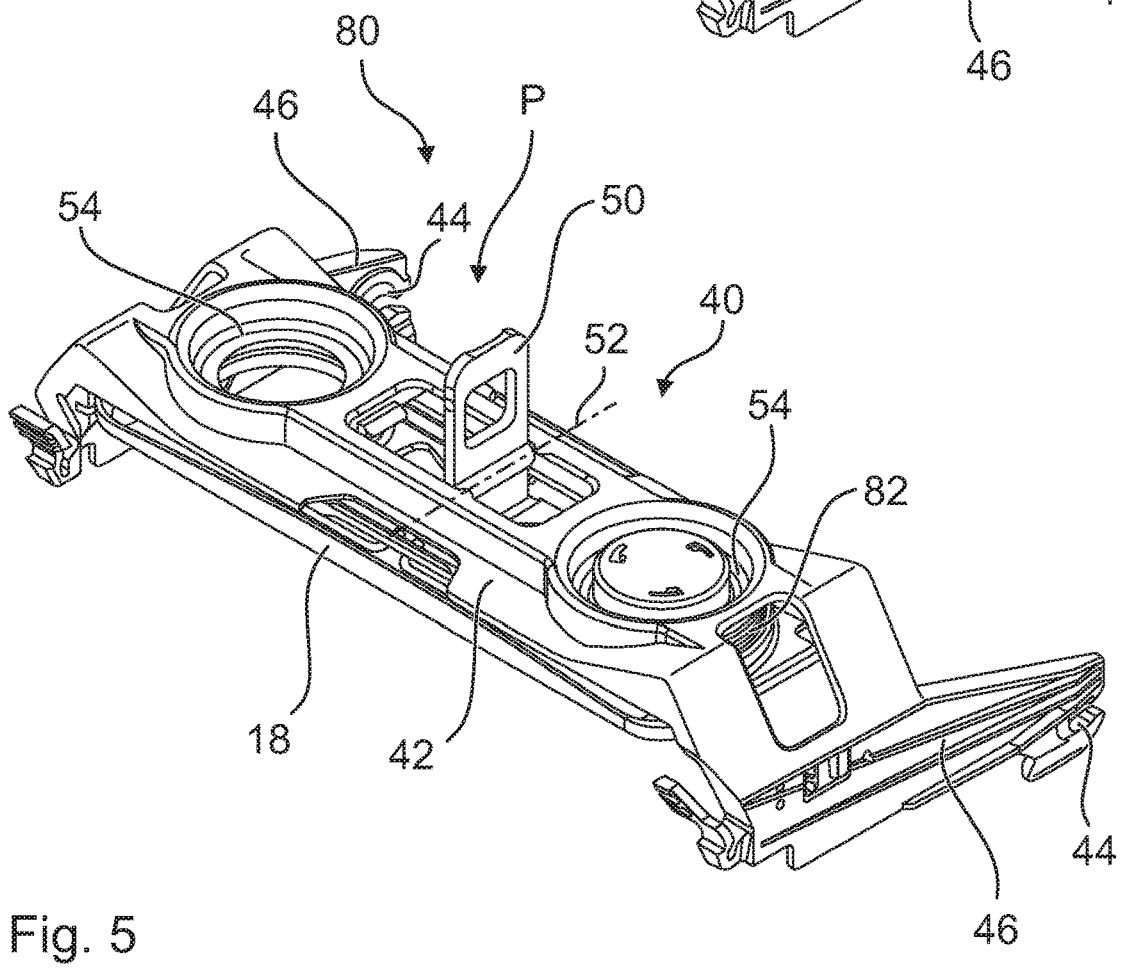
FIG. 5 is a schematic perspective view of the spring bridge breathing bag plate according to FIG. 2, wherein the locking device is in the locked position.

The spring bridge breathing bag plate system 80 according to FIGS. 2 and 3 is shown in FIGS. 4 and 5 in a perspective view. It can be clearly seen in this position that a fastening element 44 each in the form of a rotational receptacle is arranged at the free end of the cantilevers 46, i.e., at the ends of the cantilevers 46 that are facing away from the spring bridge carrier 42. The spring bridge 40 is no longer permanently riveted to a housing bottom side of a housing of a closed-circuit respirator, as in the state of the art, but rather can be rotationally connected to the housing 102 of a closed-circuit respirator 100 via two pins protruding on the inner wall of the housing lower shell 104 and the two insertable receptacles 44 at the free ends of the cantilevers 46 to one another.

The spring elements 82 of the spring bridge breathing bag plate system 80, which spring elements are configured as compression springs, are compressed as much as possible in the views shown in FIGS. 4 and 5, so that the breathing bag plate 18 is arranged directly on the bottom side of the spring bridge carrier 42. In FIG. 4, the locking device 50 of the spring bridge, which locking device is arranged at a pivot axis 52, is located in a released position F. In this released position F, the locking device 50 does not hold the breathing bag plate 18 securely, so that the breathing bag plate 18 could be moved away from the spring bridge carrier 42 because of the spring force of the spring elements 82.

In FIG. 5 the locking device 50 is located in a locked position P. In this locked position P, the locking device 50 locks the breathing bag plate 18 at the spring bridge carrier 42. In other words, the locking device 50, which is preferably configured as a snap-in element or a clamping element, extends behind, for example, a corresponding undercut of the breathing bag plate 18 and thus securely holds this breathing bag plate in a defined position under the spring bridge carrier 42. In this locked position P, the spring bridge breathing bag plate system 80 forms a very compact unit, which can be moved, especially pivoted, in a simple manner from the working position A into an opened position O. A lot of space results for the access to the then accessible breathing bag 10 of a closed-circuit respirator 100 due to the compact unit of the spring bridge breathing bag plate system 80 as well as the pivoting of the spring bridge breathing bag plate system 80 about the pivot axis of the rotating element 44.

Figure 6:
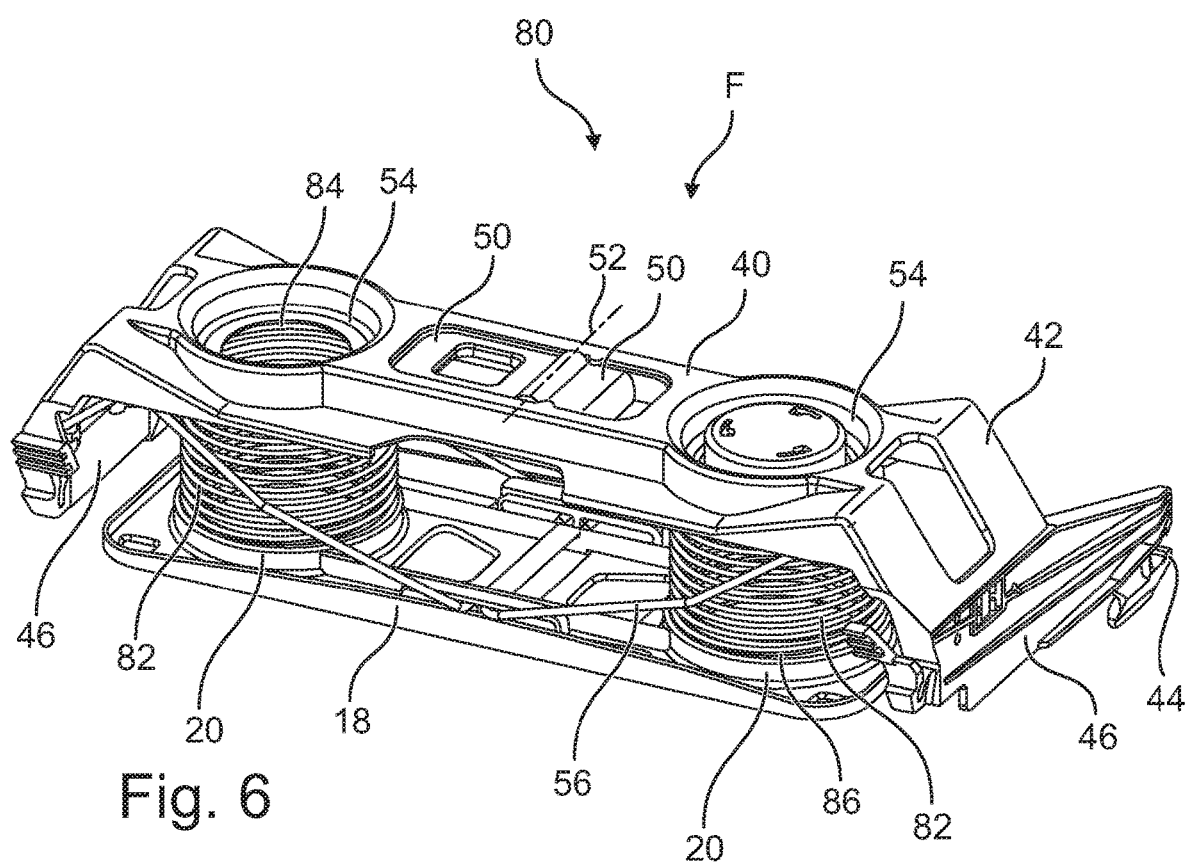
FIG. 6 is a schematic perspective view of a spring bridge breathing bag plate system according to the present invention.

FIG. 6 schematically shows the spring bridge breathing bag plate system 80 according to the embodiment of FIGS. 2 through 5 in a perspective view. The locking device 50, which is arranged pivotingly about the pivot axis 52, is located in the released position F, so that the breathing bag plate 18 is arranged at a spaced location from the spring bridge carrier 42 of the spring bridge 40 because of the spring force of the spring elements 82, which are configured as compression springs. In addition, the spring bridge breathing bag plate system 80 has a stabilizing element 56, which ensures that the breathing bag plate 18 is displaced linearly, i.e., parallel to the spring bridge carrier 42 of the spring bridge 40, both when the breathing bag plate 18 is moved in the direction of the spring bridge carrier 42 and when the breathing bag plate 18 is moved away from the spring bridge carrier 42. The stabilizing element 56 ensures that the spring elements, which are configured as compression springs, do not bend at an angle, but rather can be compressed or decompressed linearly along their spring axis.

Figure 7:
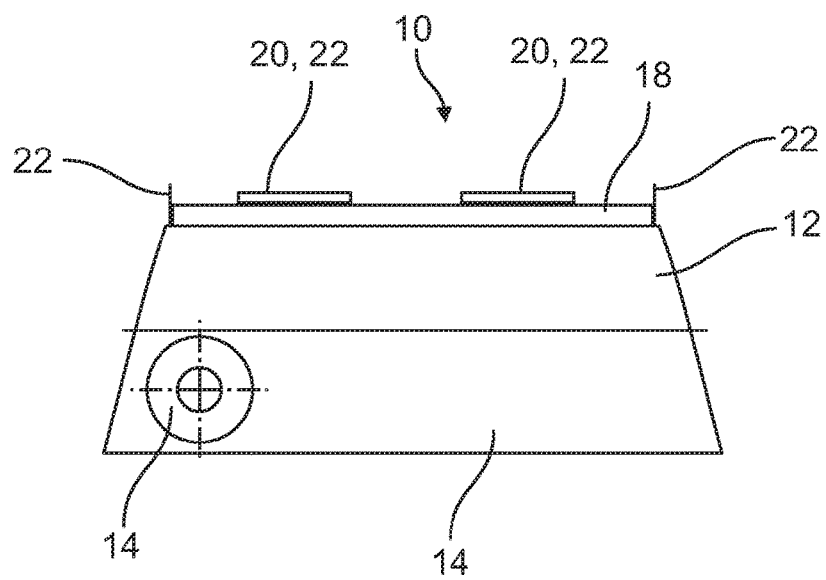
FIG. 7 is a schematic side view of a breathing bag with a breathing bag plate of a spring bridge breathing bag plate system, which breathing bag plate is arranged at the breathing bag.

FIG. 7 schematically shows in a side view a breathing bag 10 with a breathing bag plate 18 of a spring bridge breathing bag plate system 80, which breathing bag plate is arranged at the breathing bag 10. The breathing bag plate 18 has two second receiving elements 20 for the positive-locking mounting of the respective second ends of the compression springs or tension springs 82 of the spring bridge breathing bag plate system 80. The second receiving elements 20 are preferably configured as ring-shaped grooves, tubular, pot-like or sleeve-like projections 22. In addition to the positive-locking holding of the compression springs or tension springs 82, fixing elements, which are not shown, for example, in the form of small pins may be provided at the breathing bag plate 18 in order to guarantee a better hold, especially a forced fit hold, of the compression springs or tension springs 82 at the breathing bag plate 18 or at the at least one second receiving element 20 of the breathing bag plate 18. The breathing bag 10 preferably has a stable bottom side 14 and a top side 12 movable toward the stable bottom side 14. Further, ports, sockets 16 may be arranged on the bottom side 14.

Figure 8:
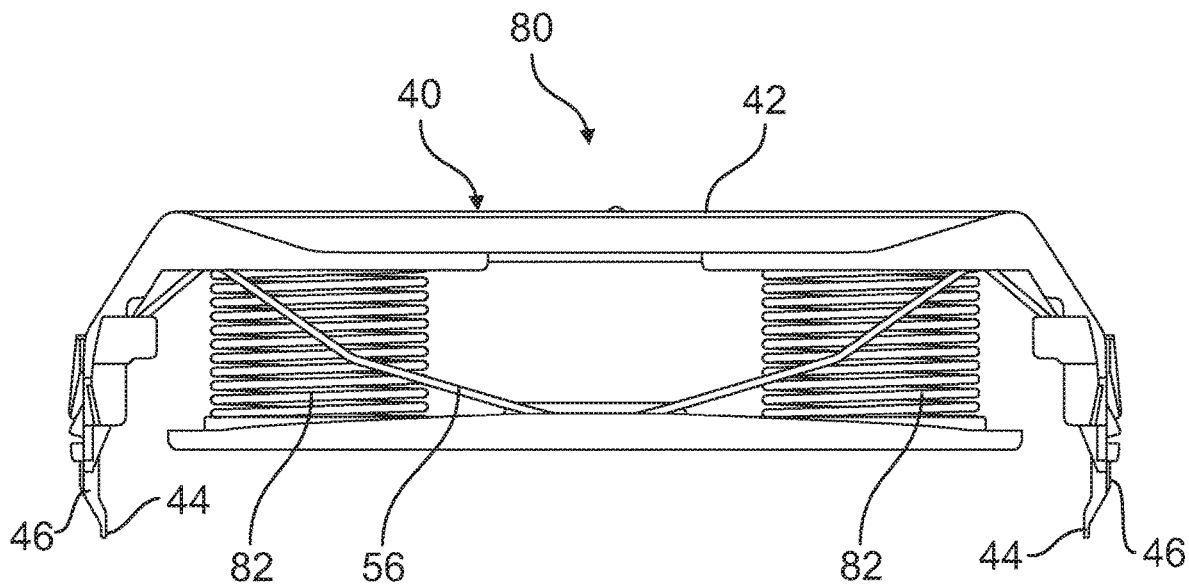
FIG. 8 is a schematic side view showing the spring bridge breathing bag plate system according to FIG. 6.
Figure 9:
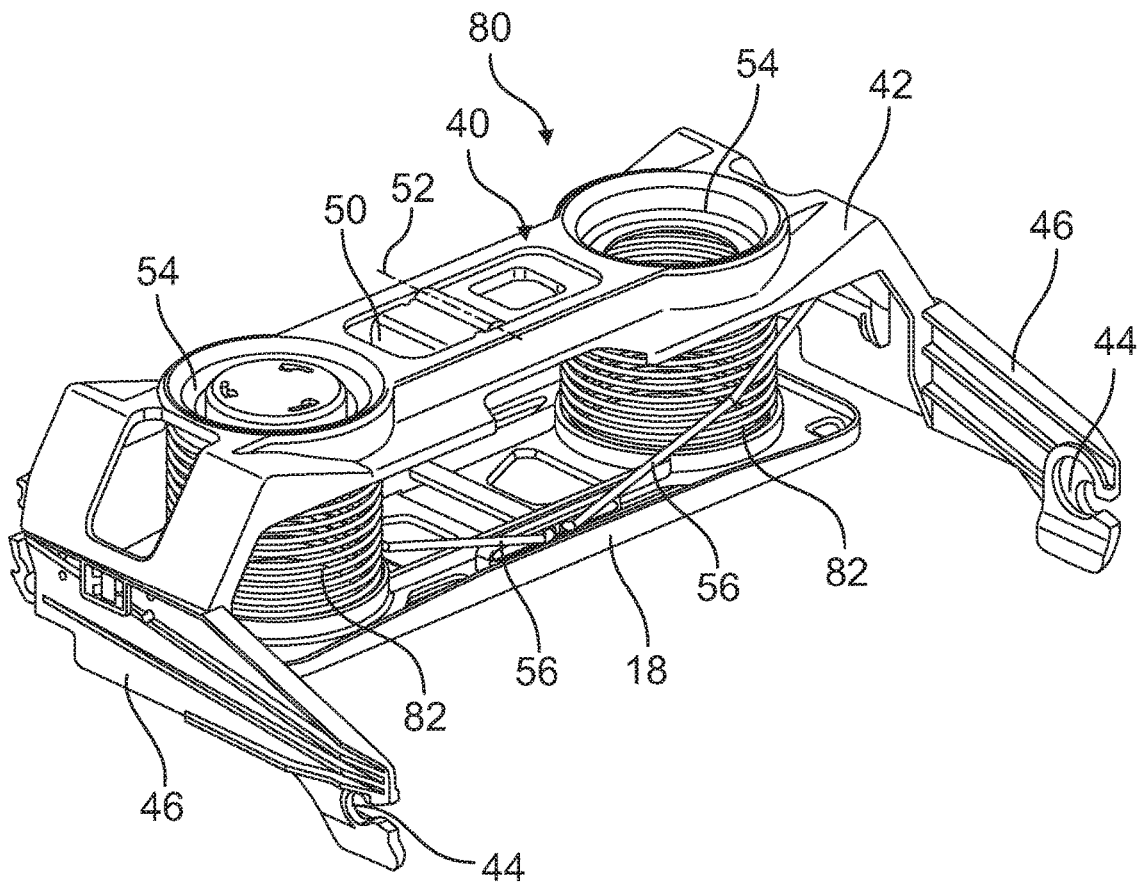
FIG. 9 is a schematic perspective view of the spring bridge breathing bag plate system according to FIG. 6.

FIG. 8 shows the spring bridge breathing bag plate system 80 according to FIG. 6 in a side view; FIG. 9 shows the spring bridge breathing bag plate system 80 according to FIG. 6 in another perspective view. The stabilizing element 56, which ensures that the breathing bag plate 18 is displaced linearly, i.e., parallel to the spring bridge carrier 42 of the spring bridge 40, in case of a filling or emptying of the breathing bag 10 of a closed-circuit respirator 100, can clearly be seen. The fastening elements 44 at the ends of the cantilevers 46 can be readily seen in FIG. 9. The fastening elements 44, rotating elements here, are used for the simple and defined pivoting of the spring bridge 40 and thus of the spring bridge breathing bag plate system 80 relative to the housing 102 of a closed-circuit respirator 100. The rotating elements 44 shown here are so-called receptacles, which can be plugged onto these counter-fastening elements 48 for the rotational movement about corresponding counter-fastening elements 48 at the inner wall of a housing lower part 104 of a housing 102 of a closed-circuit respirator 100. Correspondingly, the receptacles can also again be moved from the counter-fastening elements 48, so that the spring bridge breathing bag plate system 80 can be completely removed from the closed-circuit respirator 100.

Figure 10:
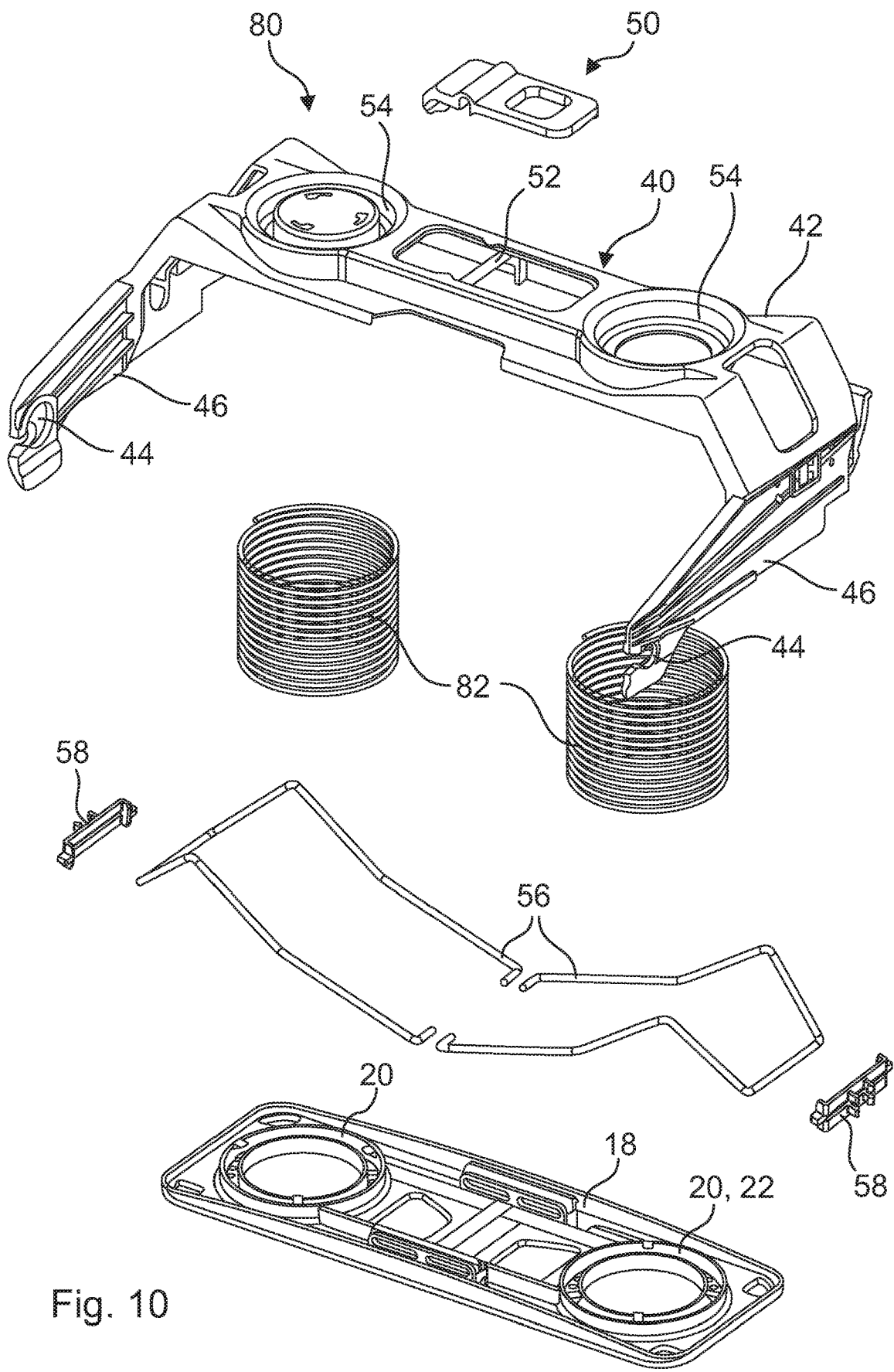
FIG. 10 is a schematic exploded view of the spring bridge breathing bag plate system according to FIG. 6.

FIG. 10 schematically shows in an exploded view the spring bridge breathing bag plate system 80 according to FIG. 6. The locking device 50 is configured as a pivoting lever and can be pivotably mounted at the pivot axis 52 of the spring bridge carrier 42. The spring elements 82 are arranged, preferably fixed between the spring bridge carrier 42 and the breathing bag plate 18. So that the spring elements 82 can be decompressed and especially compressed linearly, the stabilizing elements 56, in the form of wire straps here, are tensioned between the spring bridge carrier 42 and the breathing bag plate 18. The stabilizing elements 56 ensures that the spring elements 82, which are configured as compression springs, do not bend at an angle, but rather can be compressed or decompressed linearly along their spring axis. A uniform pressure can correspondingly be exerted via the breathing bag plate 18 onto the breathing bag 10 of a closed-circuit respirator 100.

Figure 11:
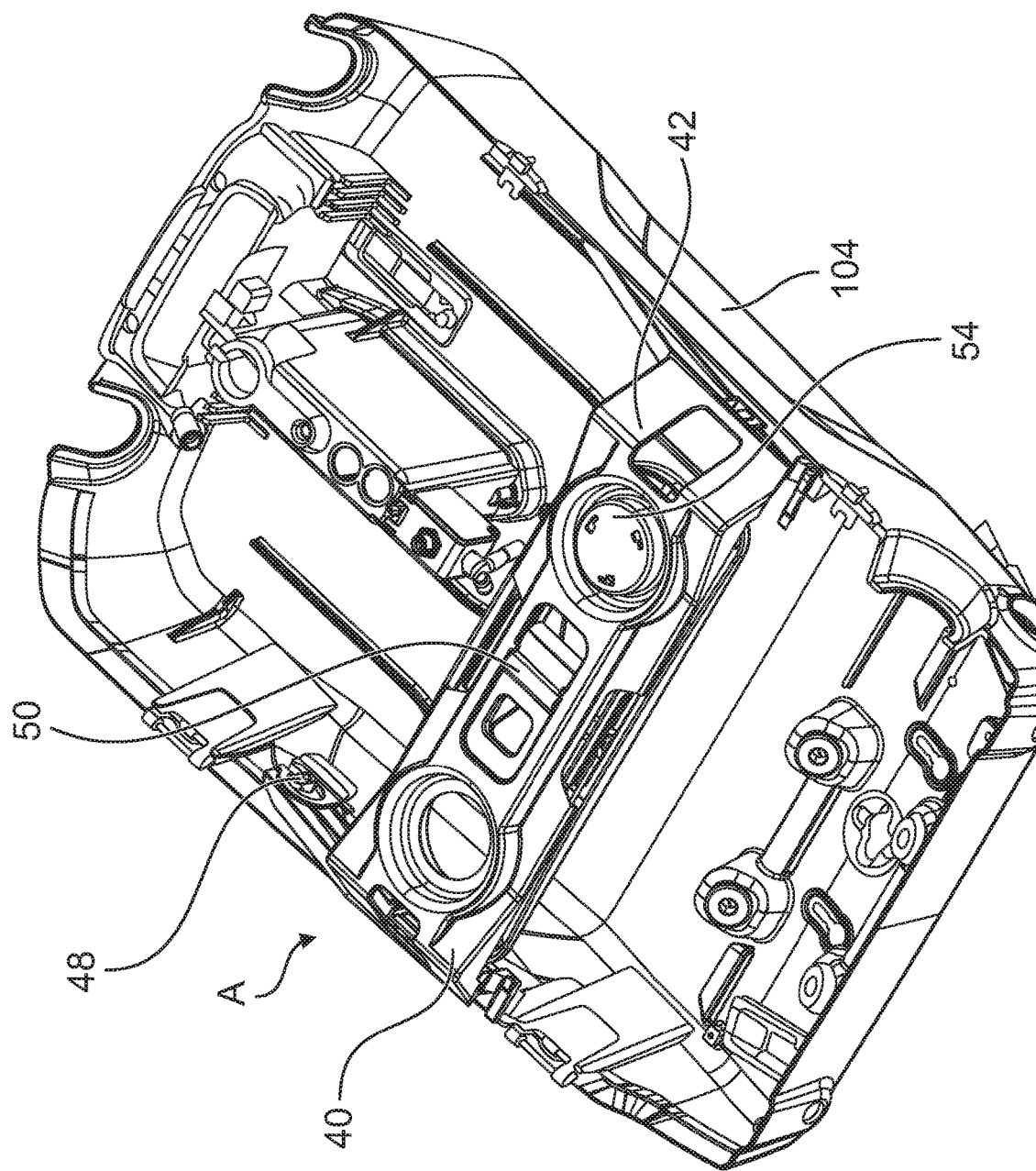
FIG. 11 is a schematic perspective view of the housing lower part of a closed-circuit respirator with a spring bridge breathing bag plate system according to the present invention in a working position.
Figure 12:
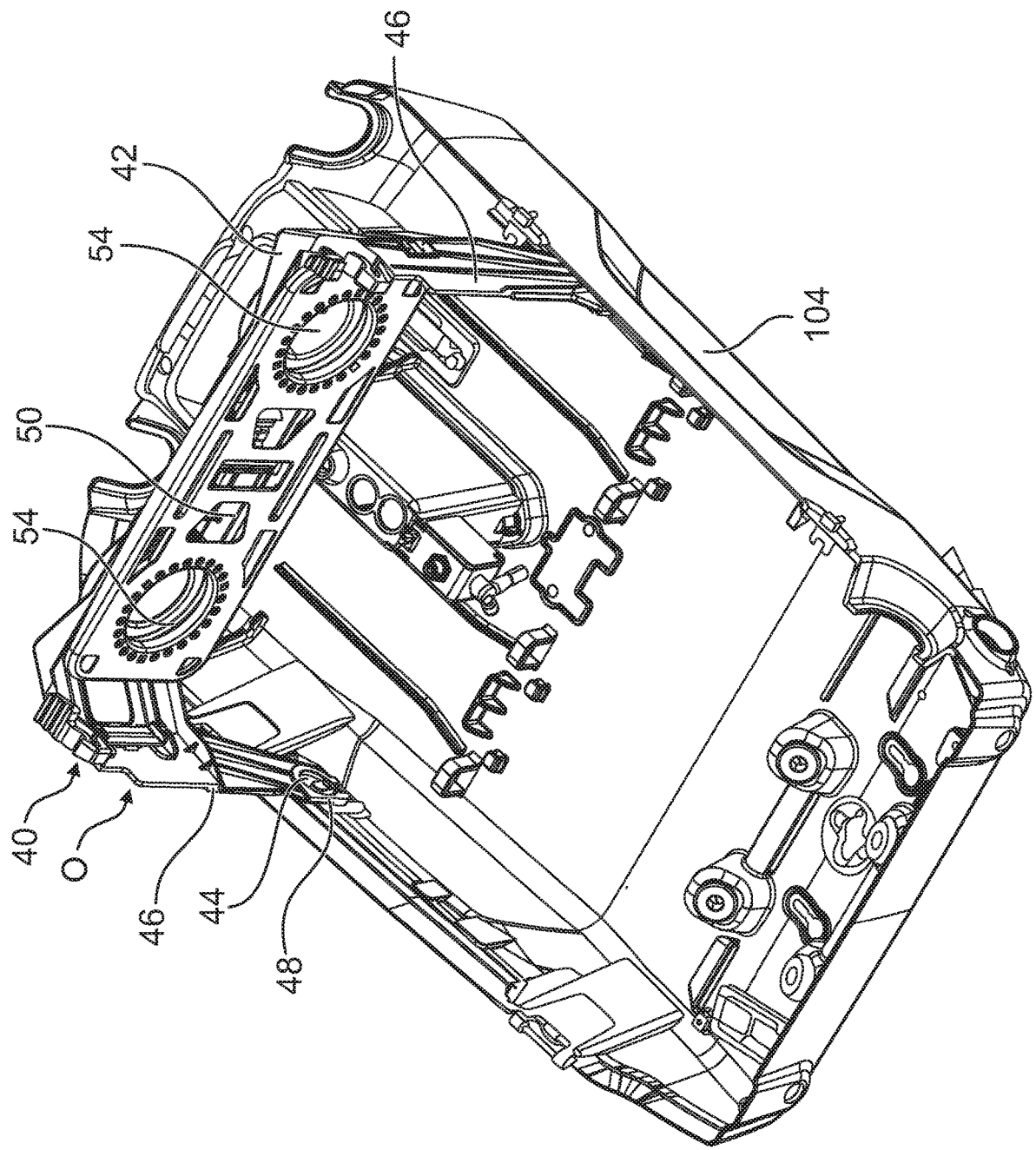
FIG. 12 is a schematic perspective view of the housing lower part according to FIG. 11, wherein the spring bridge breathing bag plate system is pivoted into an opened position.
Figure 13:
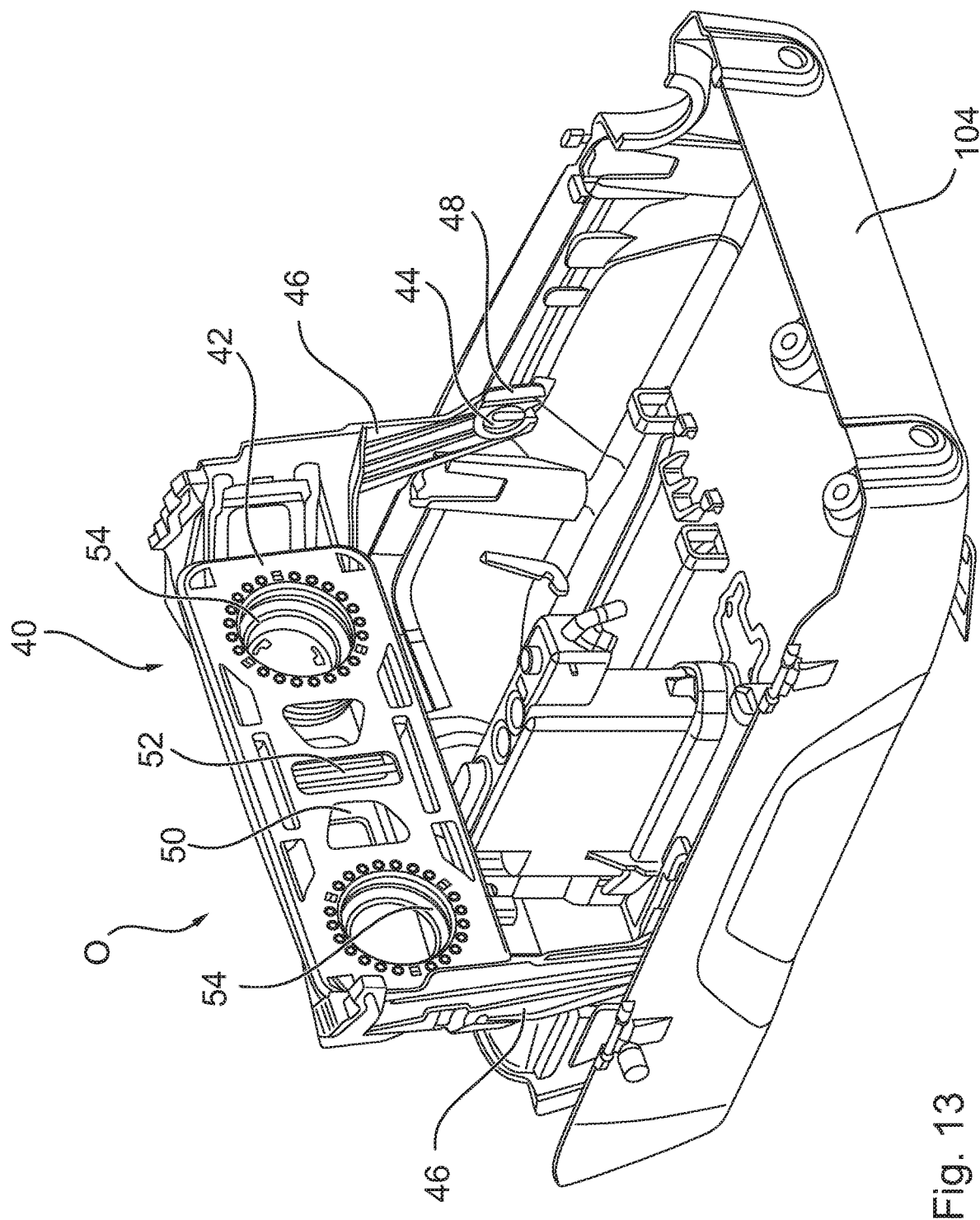
FIG. 13 is a schematic perspective view of the housing lower part according to FIG. 12, in which the spring bridge breathing bag plate system is located in an opened position.
Figure 14:
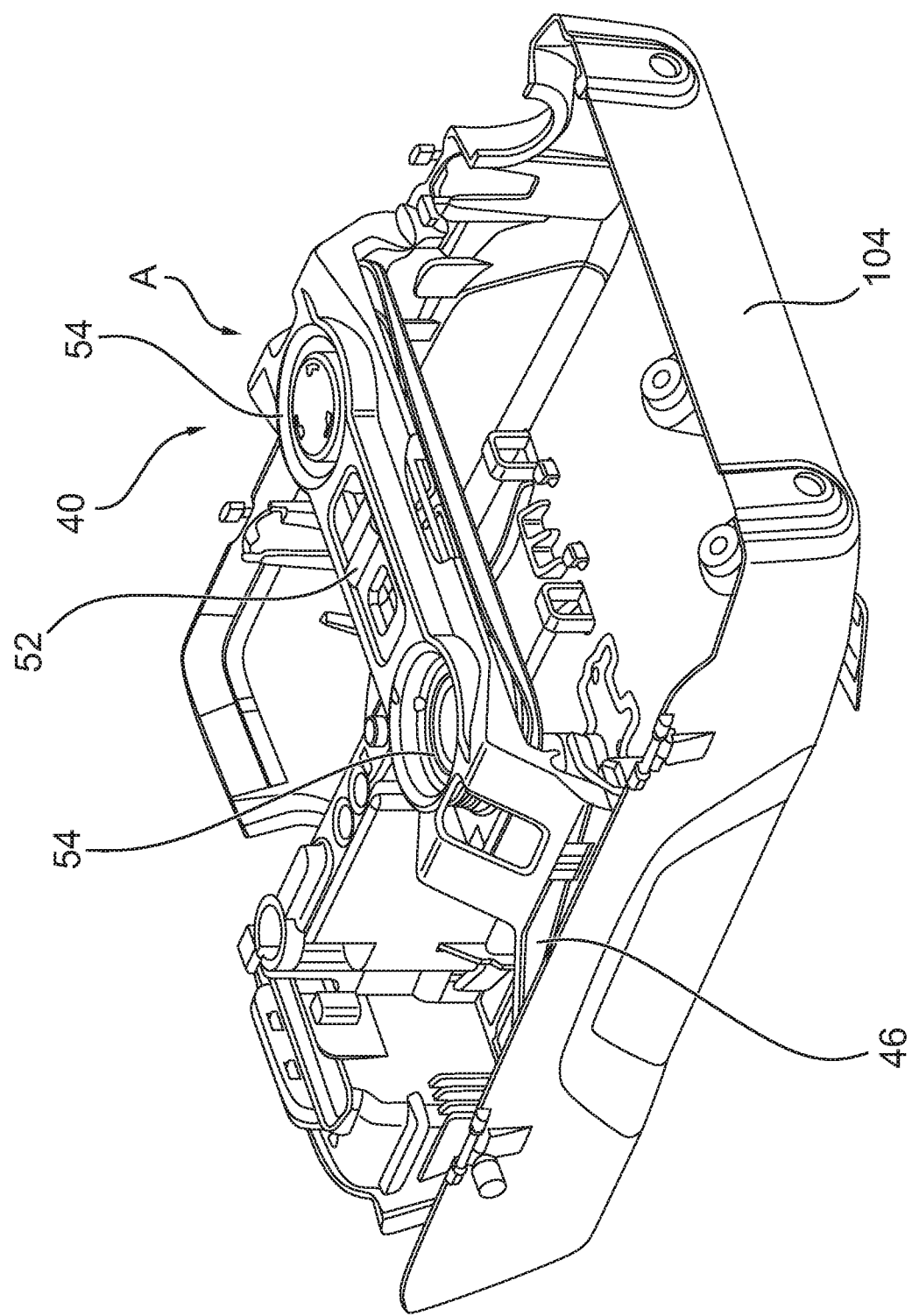
FIG. 14 is a schematic perspective view of the housing lower part of the closed-circuit respirator, wherein the spring bridge breathing bag plate system is located in a working position.
Figure 15:
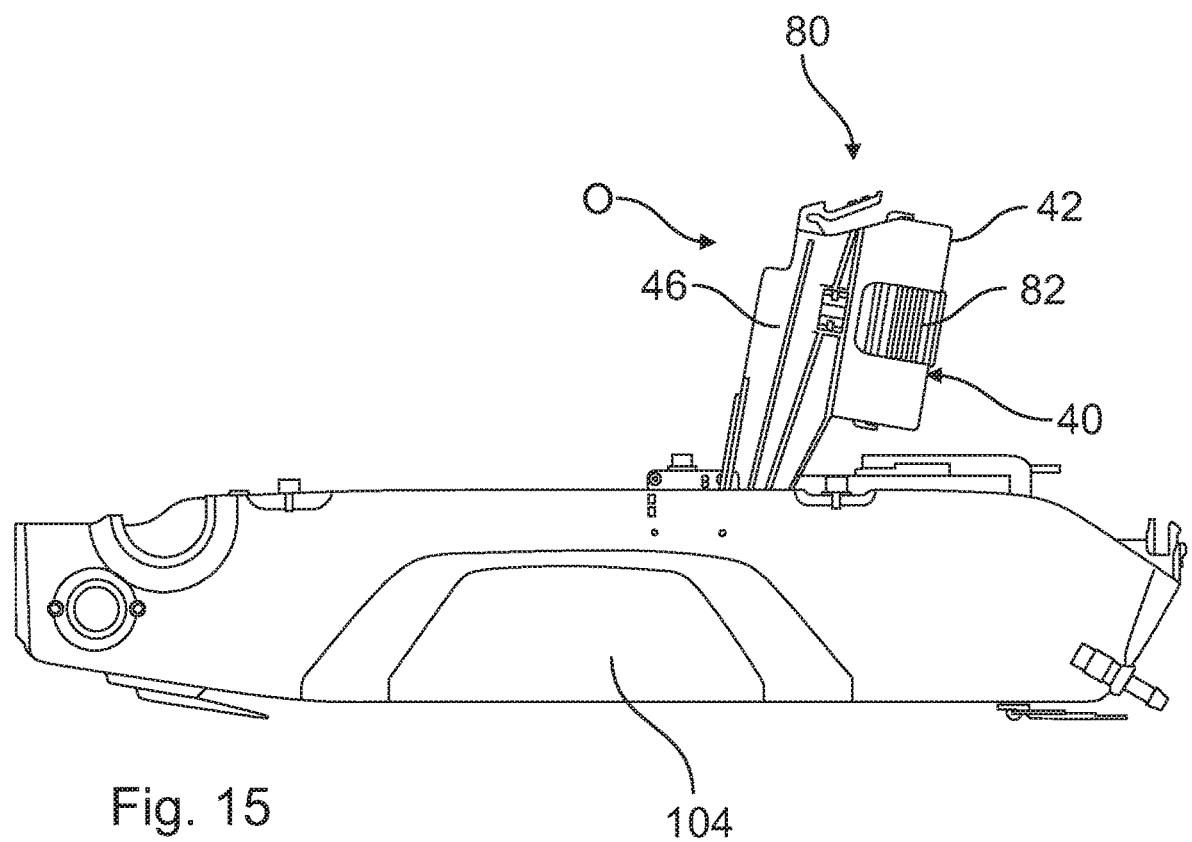
FIG. 15 is a schematic side view of the housing lower part of the closed-circuit respirator according to FIG. 11, with a spring bridge breathing bag plate system in an opened position.
Figure 16:
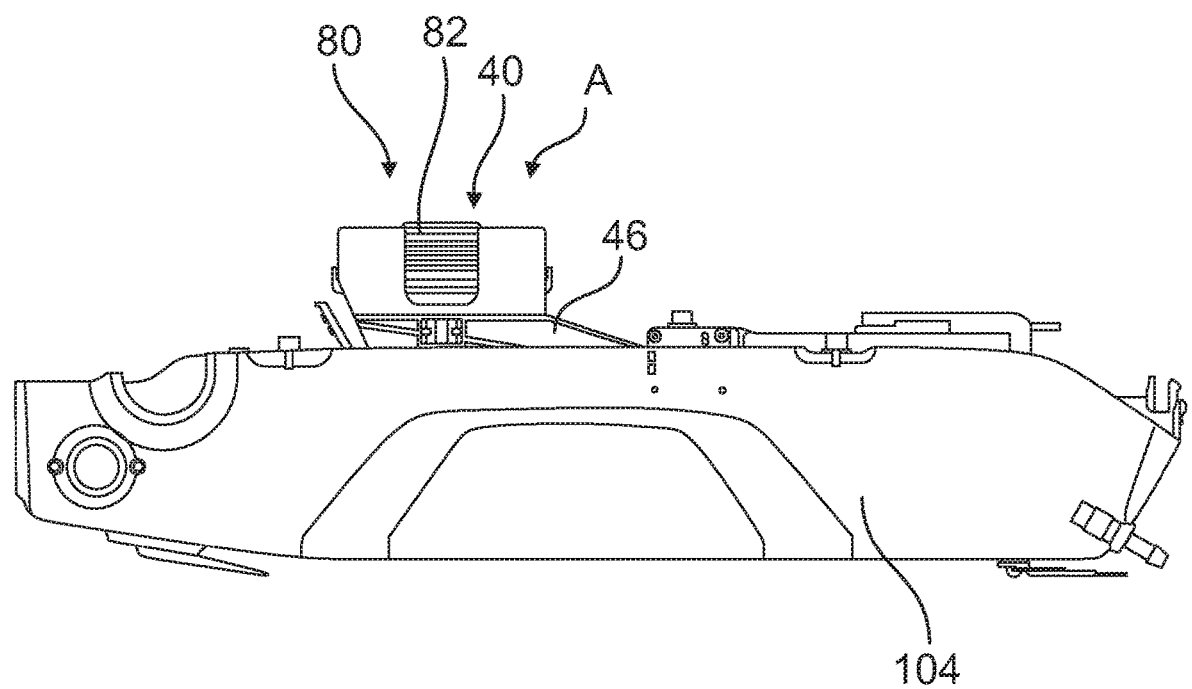
FIG. 16 is a schematic side view of the housing lower part of a closed-circuit respirator according to FIG. 11 with a spring bridge breathing bag plate system in a working position.

FIGS. 11 through 16 show different views of a housing lower part 104 of a housing 102 of a closed-circuit respirator 100 each with a spring bridge breathing bag plate system 80 according to the present invention. In FIGS. 11, 14 and 16, the spring bridge breathing bag plate system 80 is in each case located in a working position A, in FIGS. 12, 13 and 15, the spring bridge breathing bag plate system 80 is in each case located in an opened position O. In the working position A, the spring bridge 40 or the spring bridge breathing bag plate system 80 is arranged at the housing lower part 104 of the closed-circuit respirator 100 such that the spring elements 82, which are arranged between the spring bridge 40 and the breathing bag 10, can exert pressure on the breathing bag 10. In other words, in the working position A, the spring bridge 40 is used as a support of the compression springs or tension springs. In the working position A, the spring bridge 40 and thus the spring bridge breathing bag plate system 80 is arranged immovably, preferably riveted, at the closed-circuit respirator 100. In the opened position O, the spring bridge 40 and thus the spring bridge breathing bag plate system 80 are pivoted by 90° or by approximately 90° with respect to the working position A. As a result, the breathing bag 10 of a closed-circuit respirator 100 is released and can be removed in a simple manner for cleaning.

Figure 17:
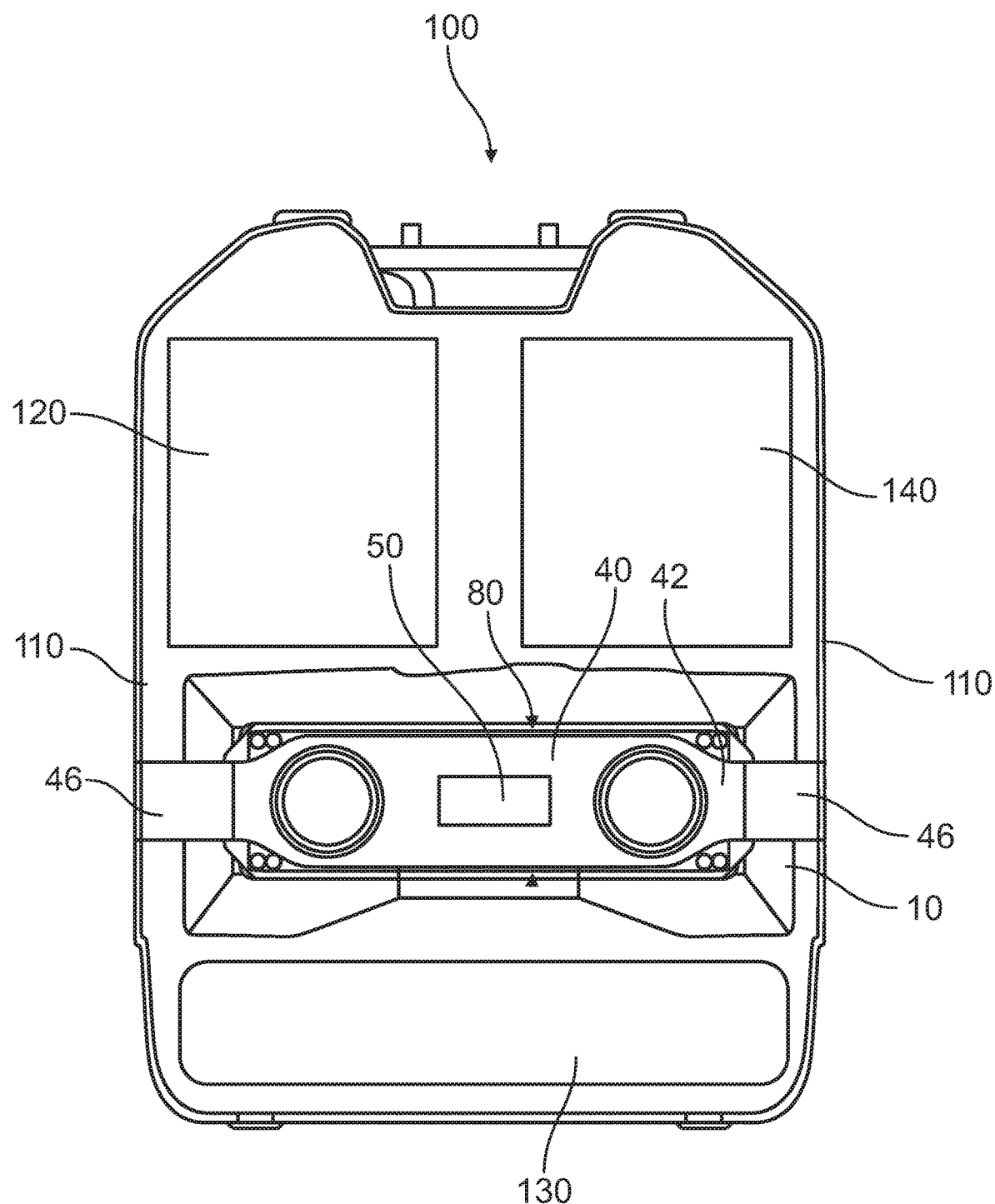
FIG. 17 is a schematic view of a closed-circuit respirator according to the present invention without housing upper part.

The spring bridge 40 and the spring bridge breathing bag plate system 80 are used for stabilizing the housing lower part 104 of the housing 102 of the closed-circuit respirator 100. This is illustrated in FIG. 17. A closed-circuit respirator

100 according to the present invention is schematically shown there. The closed-circuit respirator 100 has a housing 102 with a housing lower part 104 and with a housing upper part 106, a $CO_2$ absorber 120, a breathing bag 10, an oxygen cylinder 130 as well as a spring bridge breathing bag plate system 80 according to the present invention. The spring bridge breathing bag plate system 80 is rotationally fastened in a rotational and/or sliding manner via fastening elements 44 at the free ends of the cantilevers 46 to corresponding counter-fastening elements 108 at two opposite inner walls of the housing lower part 104.

While specific embodiments of the invention have been shown and described in detail to illustrate the application of the principles of the invention, it will be understood that the invention may be embodied otherwise without departing from such principles.

The invention claimed is:

1. A spring bridge for a spring bridge breathing bag plate system of a closed-circuit respirator, the spring bridge comprising:
   a spring bridge breathing bag plate system spring element;
   a spring bridge carrier for an arrangement of the spring bridge breathing bag plate system spring element; and
   a fastening element configured to hold the spring bridge at the closed-circuit respirator in a working position and an opened position, wherein the fastening element comprises a rotating element configured for rotatable movement of the spring bridge at and relative to the closed-circuit respirator to displace the spring bridge from the working position, in which the spring element exerts a spring force on a breathing bag, into the opened position, in which the breathing bag is released from the spring force.

2. The spring bridge in accordance with claim 1, wherein the rotating element is a rotary joint, a universal joint, an angular element, a ball and socket joint, a hinge element or a receptacle for fastening to a pin of the closed-circuit respirator.

3. The spring bridge in accordance with claim 1, further comprising a cantilever, wherein the fastening element is arranged at the cantilever, wherein the cantilever is arranged at the spring bridge carrier bent at an angle to the spring bridge carrier.

4. The spring bridge in accordance with claim 1, further comprising a holding element configured to hold the spring bridge in the working position and to hold the spring bridge in the opened position.

5. The spring bridge according to claim 4, wherein the holding element is one of a snap-in element and a clamping element.

6. The spring bridge in accordance with claim 1, wherein the spring bridge carrier has a locking device for locking a breathing bag plate of the spring bridge breathing bag plate system at the spring bridge carrier, which breathing bag plate is acted on by the spring force of the spring element of the spring bridge breathing bag plate system.

7. The spring bridge in accordance with claim 6, wherein the locking device is mounted in a pivotingly movable manner at the spring bridge carrier via a pivot axis.

8. The spring bridge in accordance with claim 7, wherein the locking device extends flatly or approximately flatly to the spring bridge carrier, in a released position, in which the breathing bag plate of the spring bridge breathing bag plate system is not held by means of the locking device at the spring bridge carrier, and the locking device extends sloped toward the spring bridge carrier in a locked position, in which the breathing bag plate of the spring bridge breathing bag plate system is held at the spring bridge carrier by means of the locking device.

9. The spring bridge in accordance with claim 1, wherein the spring bridge carrier has at least one first receiving element for arrangement of at least one first end of the spring bridge breathing bag plate system spring element.

10. The spring bridge in accordance with claim 1, wherein the fastening element is configured to be connected to the closed-circuit respirator when the spring bridge is in the working position and the opened position.

11. A spring bridge breathing bag plate system for a closed-circuit respirator, the spring bridge breathing bag plate system comprising:
   a breathing bag plate;
   a spring bridge; and
   a spring bridge breathing bag plate system spring element arranged between the breathing bag plate and the spring bridge,
   wherein the spring bridge comprises a spring bridge carrier for an arrangement of the spring bridge breathing bag plate system spring element and a fastening element configured to hold the spring bridge at the closed-circuit respirator in a working position and an opened position, wherein the fastening element comprises a rotating element configured for rotatable movement of the spring bridge at and relative to the closed-circuit respirator to displace the spring bridge from the working position, in which the spring element exerts a spring force on a breathing bag, into the opened position, in which the breathing bag is released from the spring force.

12. The spring bridge breathing bag plate system in accordance with claim 11, further comprising one or more stabilizing elements arranged between the breathing bag plate and the spring bridge carrier of the spring bridge for a defined up and down movement of the breathing bag plate in a direction away from and toward the spring bridge.

13. The spring bridge breathing bag plate system in accordance with claim 11, wherein the breathing bag plate has at least one second receiving element for arrangement of at least one second end of the spring bridge breathing bag plate system spring element.

14. The spring bridge breathing bag plate system in accordance with claim 11, wherein the breathing bag plate has a fastening device for a detachable fastening of the breathing bag plate to a breathing bag top side of a breathing bag.

15. The spring bridge breathing bag plate system in accordance with claim 11, wherein the fastening element is configured to be connected to the closed-circuit respirator when the spring bridge is in the working position and the opened position.

16. A closed-circuit respirator comprising:
   a housing comprising a housing lower part and a housing upper part;
   a $CO_2$ absorber;
   a breathing bag;
   an oxygen cylinder; and
   a spring bridge breathing bag plate system comprising:
      a breathing bag plate;
      a spring bridge; and
      a spring bridge breathing bag plate system spring element arranged between the breathing bag plate and the spring bridge,
   wherein the spring bridge comprises a spring bridge carrier for an arrangement of the spring bridge breathing bag plate system spring element and a fastening element configured to hold the spring bridge at the housing in a working position and an opened position, wherein the fastening element comprises a rotating element configured for rotatable movement of the spring bridge at and relative to the housing to displace the spring bridge from the working position, in which the spring element exerts a spring force on a breathing bag, into the opened position, in which the breathing bag is released from the spring force.

17. The closed-circuit respirator in accordance with claim 16, wherein the housing lower part has at least one counter-fastening element for the rotatable holding of the spring bridge at the closed-circuit respirator by means of the fastening element of the spring bridge carrier.

18. The closed-circuit respirator in accordance with claim 16, wherein a counter-fastening element is provided on each of two opposite sides of the housing for receiving two of the fastening elements of the spring bridge carrier.

19. The closed-circuit respirator in accordance with claim 16, wherein the breathing bag has one or more projections for positive-lockingly receiving the breathing bag plate.

* * * * *